(12) United States Patent
Tramposch et al.

(10) Patent No.: US 6,319,948 B2
(45) Date of Patent: Nov. 20, 2001

(54) RETINOID ANTAGONISTS AND USES THEREOF

(75) Inventors: Kenneth M. Tramposch; Xina Nair, both of E. Amherst, NY (US); Anne Marinier, Quebec (CA); Fred Christopher Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1 days.

(21) Appl. No.: 09/732,850

(22) Filed: Dec. 8, 2000

Related U.S. Application Data

(63) Continuation of application No. 09/363,625, filed on Jul. 29, 1999, now abandoned, which is a continuation of application No. 09/055,797, filed on Apr. 6, 1998, now abandoned.
(60) Provisional application No. 60/043,528, filed on Apr. 11, 1997.

(51) Int. Cl.$^7$ .................... A61K 31/192; C07C 63/44; C07C 69/76; C07D 233/54; C07D 333/22
(52) U.S. Cl. .................... 514/513; 514/569; 546/285; 548/343.5; 549/70; 549/434; 560/80; 560/100; 560/102; 562/490; 562/492; 562/510
(58) Field of Search ..................... 514/513, 569; 560/80, 100, 102; 562/490, 492, 510; 548/343.5; 546/285; 549/70, 435

(56) References Cited

U.S. PATENT DOCUMENTS

| | | |
|---|---|---|
| 4,876,381 | 10/1989 | Lang et al. . |
| 5,534,261 | 7/1996 | Rodgers et al. . |
| 5,618,839 | 4/1997 | Starrett, Jr. et al. . |
| 5,648,514 | 7/1997 | Johnson et al. . |

FOREIGN PATENT DOCUMENTS

| | | |
|---|---|---|
| 661259A1 | 7/1995 | (EP) . |
| WO97/09297 | 3/1997 | (WO) . |
| WO97/48672 | 12/1997 | (WO) . |

OTHER PUBLICATIONS

Y. Zasshi, "Novel Synthetic Retinoid Agonists and Antagonists," J. Of Pharmaceutical Society Of Japan, 114(11), pp. 847–862 (1994).

Mi–Ock Lee, et al, "A Synthetic Retinoid Antagonist Inhibits the Human Immunodeficiency Virus Type 1 Promoter," Proc. Natl. Acad. Sci. USA, 91(12), pp. 5632–5636 (1994).

C. Agarwal, et al, AGN193109 is a Highly Effective Antagonist of Retinoid Action in Human Ectocervical Epithelial Cells, J. Biol. Chem, 271(21), pp. 12209–12212 (1996).

A.T. Johnson, et al, "Synthesis and Characterization of a Highly Potent and Effective Antagonist of Retinoc Acid Receptors," J. Med. Chem., 38, pp. 4764–4767 (1995).

L. Eyrolles, et al, "Retinobenzoic Acids. 6. Retinoid Antagonists with a Heterocyclic Ring," J. Med. Chem., 37, pp. 1508–1517 (1994).

C. Apfel, et al, "A Retinoic Acid Receptor α Antagonist Selectively Counteracts Retinoic Acid Effects," Proc. Natl. Acad. Sci. USA, 89, pp. 7129–7133 (1992).

S. Kaneko, et al, "Retinoid Antagonists," Med. Chem. Res., 1, pp. 220–225 (1991).

H. Yoshimura, et al, "A Novel Type of Retinoic Acid Receptor Antagonist: Synthesis and Structure–Activity Relationships of Heterocyclic Ring–Containing Benzoic Acid Derivatives," J. Med. Chem., 38, pp. 3163–3173 (1995).

Mi–Ock Lee, et al, "A Novel Class of Retinoid Antagonists and Their Mechanism of Action," J. Biol. Chem., 271(20), pp. 11897–11903 (1996).

J. Ostrowski, et al, The N–Terminal Portion of Domain E of Retinoic Acid Receptors α and β is Essential for the Recognition of Retinoic Acid and Various Analogs, Proc. Natl. Acad. Sci. USA, 92, pp. 1812–1816 (1995).

*Primary Examiner*—T. A. Solola
(74) *Attorney, Agent, or Firm*—David M. Morse

(57) ABSTRACT

Retinoid antagonist compounds have been found to be useful in the prevention and/or minimization of surgical adhesion formation.

Also provided by the invention are certain novel substituted (5,6)-dihydronaphthalenyl compounds which are retinoid antagonists and possess the above-mentioned property in addition to their use as antiinflammatory agents for chronic skin inflammatory diseases, as agents for the treatment of rheumatic diseases and as agents for the treatment of various tumors as well as non-malignant proliferative skin conditions.

8 Claims, 1 Drawing Sheet

RETINOID ANTAGONISTS AND USES THEREOF

CROSS-REFERENCE TO RELATED APPLICATIONS

This is a continuation of application Ser. No. 09/363,625 filed Jul. 29, 1999 now abandoned which is a continuation of application Ser. No. 09/055,797 filed Apr. 6, 1998 now abandoned which claims the priority of U.S. Provisional Application Ser. No. 60/043,528 filed Apr. 11, 1997.

FIELD OF THE INVENTION

The present invention is directed to methods for the minimization or prevention of post-surgical adhesion formation using retinoid antagonist compounds, particularly the retinoid antagonist compounds disclosed in U.S. Pat. No. 5,618,839; see also EP 661,259 A1 published Jul. 5, 1995. The above-mentioned U.S. patent is herein incorporated by reference in its entirety.

In another aspect the present invention provides a novel series of substituted (5,6)-dihydronaphthalenyl compounds which are also potent retinoid antagonists. These compounds are useful as antiinflammatory agents for chronic skin inflammatory diseases such as psoriasis and atopic dermatitis, as agents for the treatment of rheumatic diseases such as rheumatoid arthritis, as antitumor agents for the treatment of various tumors as well as non-malignant proliferative skin conditions and as agents for the minimization or prevention of post-surgical adhesion formation.

BACKGROUND OF THE INVENTION

Retinoic acid and its natural and synthetic analogs exert a wide array of biological effects. They have been shown to affect cellular growth and differentiation and are promising drugs for the treatment of several cancers.

U.S. Pat. No. 5,618,839 and EP 661,259 A1 published Jul. 5, 1995 disclose a series of substituted (5,6)-dihydronapthalenyl compounds of the formula

I or nontoxic pharmaceutically acceptable salts, physiologically hydrolyzable esters or solvates thereof, in which X is —O—CO—, —NH—CO—, —CS—NH—, —CO—O—, —CO—NH—, —COS—, —SCO—, —SCH$_2$—, —CH$_2$—CH$_2$—, —C≡—C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$alkyl, hydroxy, C$_{1-6}$-alkyloxy or nitro;

n is zero or one;

R$^4$ is —(CH$_2$)$_t$—Y, C$_{1-6}$alkyl, or C$_{3-6}$cycloalkyl;

R$^1$ is —CO$_2$Z, C$_{1-6}$alkyl, CH$_2$OH, —CONHR$^y$, or CHO;

R$^2$ and R$^3$ are independently hydrogen or C$_{1-6}$alkyl;

R$^a$ and R$^b$ are independently hydrogen or C$_{1-6}$alkyl; but when n is one, R$^a$ and R$^b$ together can form a radical of the formula Y is phenyl or naphthyl and both radicals can be optionally substituted with one to three same or different C$_{1-6}$ alkyl or halogen groups;

Y is naphthyl or phenyl, both radicals can be optionally substituted with one to three same or different C$_{1-6}$alkyl or halogen;

Z is hydrogen or C$_{1-6}$alkyl;

R$^5$, R$^6$ and R$^y$ are independently hydrogen or C$_{1-6}$alkyl; and t is zero to six.

These compounds are reported to have retinoid-like activity and to be useful for preventing and/or treating various skin disorders such as acne, psoriasis and damage from irradiation, for treatment of various tumors and non-malignant proliferative skin diseases and for treatment of rheumatic diseases such as rheumatoid arthritis.

The present inventors have discovered that certain compounds included within the scope of EP 661,259A1 and U.S. Pat. No. 5,618,839 are retinoid antagonists, i.e., they bind to all three RAR retinoic acid receptor subtypes (α, β and γ) but do not activate at least two of the three subtypes when tested in a standard transactivation assay. These retinoid antagonist compounds have the general formula

IA or nontoxic pharmaceutically acceptable salts, physiologically hydrolyzable esters or solvates thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$ alkyl, hydroxy, C$_{1-6}$alkyloxy or nitro;

n is zero or one;

R$^4$ is —(CH$_2$)$_t$—Y;

R$^1$ is —CO$_2$Z, —C$_{1-6}$ alkyl, CH$_2$OH, —CONHR$^y$ or CHO;

R$^2$ and R$^3$ are independently hydrogen or C$_{1-6}$ alkyl;

R$^a$ and R$^b$ are independently hydrogen or C$_{1-6}$ alkyl; but when n is one, R$^a$ and R$^b$ together can form a radical of the formula Z is hydrogen or $C_{1-6}$ alkyl;

$R^5$, $R^6$ and $R^y$ are independently hydrogen or $C_{1-6}$ alkyl; and t is zero to six.

U.S. Pat. No. 5,534,261 discloses that retinoids, particularly all-trans retinoic acid, can be used to minimize or prevent adhesion formation following surgery. There is no illustration or suggestion, however, that a retinoid antagonist compound would have this same utility.

Published patent application WO 97/09297 discloses retinoid antagonist compounds of the general formula

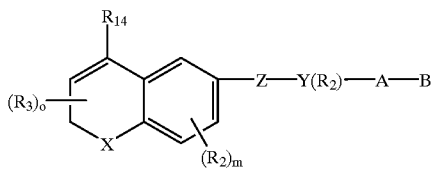

III wherein X is S, O or $NR^1$ where $R^1$ is H or alkyl of 1–6 carbons, or X is $[C(R_1)_2]_n$ where $R_1$ is independently H or alkyl of 1 to 6 carbons, and n is 0, 1 or 2;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is 0, 1, 2 or 3;

o is 0, 1, 2 or 3;

Z is —C≡C—,
—N=N—,
—N=$CR_1$—,
—$CR_1$=N,
—($CR_1$=$CR_1$)$_{n'}$ where n' is 0 or an integer of 1–5,
—CO—$NR_1$—,
—CS—$NR_1$—,
—$NR_1$—CO,
—$NR_1$—CS,
—COO—,
—OCO—,
—CSO—, or
—OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrazolyl, said phenyl and heteroaryl groups being optionally substituted with one or two $R_2$ groups, or when Z is —($CR_1$=$CR_1$)$_{n'}$ and n' is 3, 4 or 5, then Y represents a direct valence bond between said ($CR_1$=$CR_1$)$_{n'}$ group and B;

A is $(CH_2)_q$ where q is 0 or an integer of 1–5, lower branched chain alkyl having 3–6 carbons, cycloalkyl having 3–6 carbons, alkenyl having 2–6 carbons and 1 or 2 double bonds, or alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, —$CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group having 1–5 carbons, $R_8$ is an alkyl group of 1 to 10 carbons, or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$, is lower alkyl, phenyl or lower alkylphenyl, $R_{12}$ is lower alkyl, and $R_{13}$ is a divalent alkyl radical of 2–5 carbons; and $R_{14}$ is $(R_{15})_r$-phenyl, $(R_{15})_r$-naphthyl or $(R_{15})_r$-heteroaryl where the heteroaryl group has 1 to 3 heteroatoms selected from the group consisting of O, S and N, r is 0 or an integer of 1–5; and $R_{15}$ is independently H, F, Cl, Br, I, $NO_2$, $N(R_8)_2$, $N(R_8)COR_8$, $NR_8(CON(R_8)_2$, OH, $OCOR_8$, $OR_8$, CN, an alkyl group having 1 to 10 carbons, fluoro substituted alkyl group having 1 to 10 carbons, an alkenyl group having 2 to 10 carbons and 1 to 3 double bonds, alkynyl group having 2–10 carbons and 1 to 3 triple bonds, or a trialkylsilyl or trialkylsilyloxy group where the alkyl groups independently have 1 to 6 carbons.

Also disclosed in this publication as retinoid antagonist compounds are compounds of the general formula

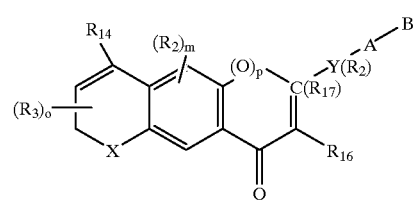

IV wherein X is S, O or $NR^1$ where $R^1$ is H or alkyl of 1–6 carbons, or

X is $[C(R_1)_2]_n$, where $R^1$ is independently H or alkyl of 1 to 6 carbons, and n is an integer between 0 and 2;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

$R_{16}$ is H, lower alkyl of 1 to 6 carbons;

$R_{17}$ is H, lower alkyl of 1 to 6 carbons, OH or $OCOR_{11}$ and p is zero or 1, with the proviso that when p is 1 then there is no $R_{17}$ substituent group, and m is an integer between 0 and 2.

The above-mentioned retinoid antagonist compounds are said to be useful for preventing certain undesired side effects of retinoids which are administered for the treatment or prevention of certain diseases or conditions. They are also said to be useful in the treatment of acute or chronic toxicity resulting from overdose or poisoning by retinoid drugs or Vitamin A.

The present inventors have surprisingly found that retinoid antagonist compounds, particularly the retinoid antagonists disclosed above which are generically taught in EP 661,259 A1 and in U.S. Pat. No. 5,618,839, have utility in preventing or minimizing post-surgical adhesion formation and, in fact, are significantly more active for this use than the retinoid agonists described in U.S. Pat. No. 5,534,261.

In another aspect, the present inventors have prepared a novel series of substituted (5,6)-dihydronaphthalenyl compounds which also are potent retinoid antagonists. These new compounds display the utilities of the retinoid antagonist compounds described in U.S. Pat. No. 5,618,839 and EP 661,259 A1, and also possess the ability to prevent or minimize post-surgical adhesion formation. This new series of retinoid antagonists is generically defined by the formula

II

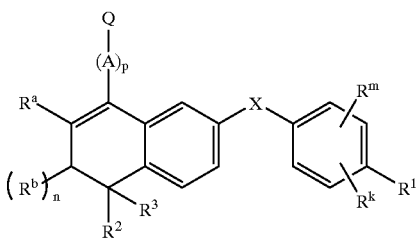

or nontoxic pharmaceutically acceptable salts, physiologically hydrolyzable esters or solvates thereof, in which X is —O—CO—, —NH—CO—, —CS—NH, —CO—O—, —CO—NH—, —COS—, —SCO—, —$SCH_2$—, —$CH_2$—$CH_2$—, —C≡C—, —$CH_2$—NH—, —$COCH_2$—, —NHCS—, —$CH_2S$—, —$CH_2O$—, —$OCH_2$—, —$NHCH_2$— or —$CR^5$=$CR^6$—;

$R^m$ and $R^k$ are independently hydrogen, halogen, $C_{1-6}$ alkyl, hydroxy, $C_{1-6}$ alkyloxy or nitro;

n is zero or one;

A is —$NH(CH_2)_m$—, —S—, —SO—, —$SO_2$—, —O—, —C≡C—, —$CR^8R^9$, —$CR^8$=$CR^9$—, phenyl, phenyl substituted by a $C_{1-6}$ alkyl, $C_{1-6}$ alkoxy, halogen, $CO_2R^8$, —$(CH_2)_mOR^8$, —$(CH_2)_mNR^9R^8$, or —$COR^{10}$ group, naphthyl, naphthyl substituted by a $C_{1-6}$ alkyl, $C_{1-6}$ alkoxy, halogen, $CO_2R^8$, —$(CH_2)_mOR^8$, —$(CH_2)_mNR^8R^9$ or —$COR^{10}$, or heteroaryl;

Q is phenyl, naphthyl or heteroaryl, said phenyl, naphthyl or heteroaryl group being optionally substituted by one to three same or different $C_{1-6}$ alkyl, $C_{1-6}$ fluoroalkyl, $C_{1-6}$ alkoxy, halogen, $CO_2R^{11}$, —$(CH_2)_qOR^{11}$, —$(CH_2)_qNR^{11}R^{12}$, —$NHCOR^{13}$ or —$COR^{13}$ with the proviso that when A is —S—, —SO—, —$SO_2$— or —O—, then Q is a phenyl, naphthyl or heteroaryl group substituted by one to three halogen, $C_{1-6}$ fluoroalkyl, $CO_2R^{11}$, —$(CH_2)_qOR^{11}$, —$(CH_2)_qNR^{11}R_{12}$, —$NHCOR^{13}$ or —$COR^{13}$;

$R^5$ and $R^6$ are each independently hydrogen or $C_{1-6}$ alkyl;

$R^8$ and $R^9$ are each independently hydrogen or $C_{1-6}$ alkyl;

$R^{10}$ and $R^{13}$ are each independently hydrogen, $C_{1-6}$ alkyl or $C_{1-6}$ fluoroalkyl;

$R^{11}$ and $R^{12}$ are each independently hydrogen or $C_{1-6}$ alkyl;

$R^a$ and $R^b$ are independently hydrogen or $C_{1-6}$ alkyl; but when n is one, $R^a$ and $R^b$ together can form a radical of the formula

Z is hydrogen, $C_{1-6}$ alkyl, benzyl, p-methoxybenzyl, allyl or trimethylsilylethyl;

m and q are independently 0 to 2;

p is 0 or 1 with the proviso that when p is 0 then Q is phenyl, naphthyl or heteroaryl substituted by one to three —$(CH_2)_qOR^{11}$, —$(CH_2)_qNR^{11}R^{12}$, or —$COR^{13}$ $R^2$ and $R^3$ are each independently hydrogen or $C_{1-6}$ alkyl;

$R^1$ is —$CO_2Z$, $C_{1-6}$ alkyl, —$CH_2OH$, —$CONHR^7$ or CHO;

$R^7$ is hydrogen or C1-6 alkyl;

provided that when X is —C≡C—, A is not —$CR^8$=$CR^9$— or —C≡C—.

The novel compounds of formula II are distinguished from those in WO 97/09297 by the presence of the linking group "A" between the core skeleton and the terminal aryl or heteroaryl substituent.

U.S. Pat. No. 5,648,514 discloses retinoids of the formula

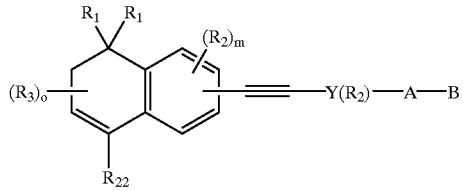

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the dihydronaphthalene nucleus;

m is an integer having the value of 0–3;

o is an integer having the value 0–3;

Y is a phenyl group, or heteroaryl selected from a group consisting of pyridyl, thienyl, furyl, pyridazinyl, pyrimidinyl, pyrazinyl, thiazolyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $—CH_2OH$, $—CH_2OR_{11}$, $—CH_2OCOR_{11}$, CHO, $CH(OR_{12})_2$, $CHOR_{13}O$, $—COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R^{13}$ is divalent alkyl radical of 2–5 carbons and $R_{22}$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl, $C_1$–$C_{10}$alkyl, naphthyl-$C_1$–$C_{10}$ alkyl, $C_1$–$C_{10}$-alkenylphenyl having 1 to 3 double bonds, $C_1$–$C_{10}$-alkenylphenyl having 1 to 3 triple bonds, phenyl-$C_1$–$C_{10}$alkenyl having 1 to 3 double bonds, phenyl-$C_1$–$C_{10}$alkynyl having 1 to 3 triple bonds, hydroxy alkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds, where the acyl group is represented by $COR_{14}$, CN, $CON(R_1)_2$, $(CH_2)_pCO_2R_8$ where p is an integer between 0 to 10, or $R_{22}$ is aminoalkyl or thioalkyl of 1 to 10 carbons, or a 5 or 6 membered heteroaryl group optionally substituted with a $C_1$ to $C_{10}$ alkyl group having 1 to 3 heteroatoms, said heteroatoms being selected from a group consisting of O, S, and N, or $R_{22}$ is represented by $(CH_2)_pXR_1$ or by $(CH_2)_pNR_1R_2$; where X is O or S, the $R_{14}$ group is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, or naphthyl-$C_1$–$C_{10}$alkyl The novel compounds of formula II are distinguished from those in U.S. Pat. No. 5,648,514 by the nature of the linking group "X" which is not C≡C linked to the central benzene ring when A is $—CR^8=CR^9—$ or $—C≡C—$.

Published patent application WO 97/48672 discloses retinoids of the formula

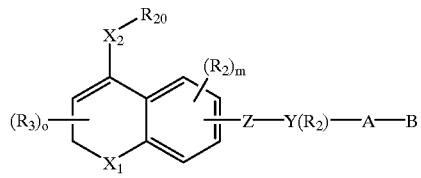

Formula 5 wherein $X_1$ is $[C(R^1)_2]_n$ where $R_1$ is independently H or alkyl of 1 to 6 carbons, and n is an integer between 0 to 2;

Z is —N=N—,
—N(O)=N—,
—N=N(O)—,
—N=CR$_1$—,
—CR$_1$=N,
—(CR$_1$=CR$_1$)$_{n'}$— where n' is an integer having the value 0–5,
—CO—NR$_1$—.
—CS—NR$_1$—.
—NR$_1$—CO,
—NR$_1$—CS—,
—COO—,
—OCO—,
—CSO—,
—OCS—,
—CO—CR$_1$=CR$_1$—;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —(CR$_1$=CR$_1$)$_{n'}$— and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $—CH_2OH$, $—CH_2OR_{11}$, $—CH_2OCOR_{11}$, CHO, $CH(OR_{12})_2$, $CHOR_{13}O$, $—COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R^{11}$ is lower alkyl, phenyl or lower alkylphenyl, $R_{12}$ is lower alkyl, and $R_{13}$ is divalent alkyl radical of 2–5 carbons;

$X_2$ is O, S, SO or $SO_2$, and $R_{20}$ is $Si(C_{1-6}alkyl)_3$, $R_{14}$, $COR_{14}$, $SO_2R_{21}$, where $R_{14}$ is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$-alkyl, naphthyl-$C_1$–$C_{10}$-alkyl, or $R_{20}$ is hydroxyalkyl, aminoalkyl or thioalkyl having 1 to 10 carbons, and $R_{21}$ is alkyl of 1 to 10 carbons, fluoroalkyl of 1 to 10 carbons, or carbocyclic aryl selected from the group consisting of phenyl, $C_1$–$C_{10}$-alkylphenyl and phenyl-$C_1$–$C_{10}$-alkyl, and retinoids of the formula Formula 6

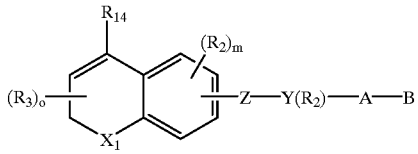

wherein $X_1$ is $[C(R_1)_2]_n$ where $R_1$ is independently H or alkyl of 1 to 6 carbons, and n is an integer between 0 and 2;

Z is —N=N—,
—N(O)=N—,
—N=N(O)—,
—N=$CR_1$—,
—$CR_1$=N,
—($CR_1$=$CR_1$)$_{n'}$— where n' is an integer having the value 0–5,
—CO—$NR_1$—.
—CS—$NR_1$—.
—$NR_1$—CO,
—$NR_1$—CS—,
—COO—,
—CSO—,
—OCS—,
—CO—$CR_1$=$CR_1$—;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —($CR_1$=$CR_1$)$_{n'}$— and n' is 3, 4 or 5 then Y represents a direct valence bond between said ($CR_2$=$CR_2$)$_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, —$CH_2OR_{11}$, —$CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-substituted alkyl of 1–6 carbons, $(R_{15})_r$-substituted alkenyl of 1–6 carbons and 1 or 2 double bonds, $(R_{15})_r$-substituted alkynyl of 1–6 carbons and 1 or 2 triple bonds, $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, OCOR, ORE, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl or (trialkyl) silyloxy group where the alkyl groups independently have 1 to 6 carbons.

The novel compounds of formula II may be distinguished from those in WO 97/48672, formula 5, by the nature of the linking group "A" versus "$X_2$". The formula II compounds may be distinguished from those in WO 97/48672, formula 6, by the inclusion of the linking group "A" between the core skeleton and the terminal aryl or heteroaryl substituent.

SUMMARY OF THE INVENTION

The present invention provides a method for the minimization or prevention of post-surgical adhesion formation between organ surfaces comprising administering an effective amount of a retinoid antagonist for a period of time sufficient to permit tissue repair.

In a preferred embodiment the retinoid antagonist used in the above method is a compound having the general formula

IA

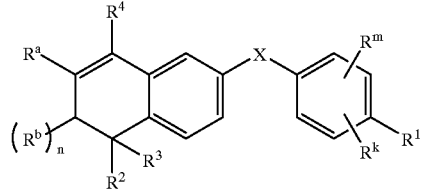

or a nontoxic pharmaceutically acceptable salt, physiologically hydrolyzable ester and solvate thereof, in which X is —O—CO—, —NH—CO—, —CSNH, —CO—O—, —CO—NH—, —COS—, —SCO—, —$SCH_2$—, —$CH_2$—$CH_2$—, —C≡—C, —$CH_2$—NH—, —$COCH_2$—, —NHCS—, —$CH_2S$—, —$CH_2O$—, —$OCH_2$—, —$NHCH_2$— or —$CR^5$=$CR^6$—;

$R^m$ and $R^k$ are independently hydrogen, halogen, $C_{1-6}$ alkyl, hydroxy, $C_{1-6}$alkyloxy or nitro;

n is zero or one;

$R^4$ is —$(CH_2)_r$—Y;

$R^1$ is —$CO_2Z$, —$C_{1-6}$ alkyl, $CH_2OH$, —$CONHR^y$ or CHO;

$R^2$ and $R^3$ are independently hydrogen or $C_{1-6}$ alkyl;

$R^a$ and $R^b$ are independently hydrogen or $C_{1-6}$ alkyl; but when n is one, $R^a$ and $R^b$ together can form a radical of the formula

Y is phenyl or naphthyl and both radicals can be optionally substituted with one to three same or different $C_{1-6}$ alkyl or halogen groups;

Z is hydrogen or $C_{1-6}$ alkyl;

$R^5$, $R^6$ and $R^y$ are independently hydrogen or $C_{1-6}$ alkyl; and t is zero to six.

In another aspect, the present inventors have prepared a novel series of substituted (5,6)-dihydronaphthalenyl compounds which also are potent retinoid antagonists. These new compounds display the utilities of the retinoid antagonist compounds described in U.S. Pat. No. 5,618,839 and EP 661,259 A1, and also possess the ability to prevent or minimize post-surgical adhesion formation. This new series of retinoid antagonists is generically defined by the formula

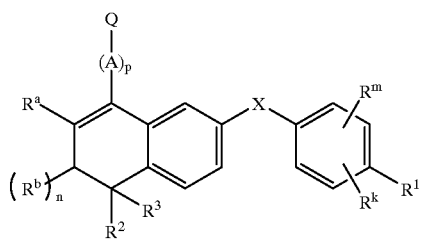

II or nontoxic pharmaceutically acceptable salts, physiologically hydrolyzable esters or solvates thereof, in which X is —O—CO—, —NH—CO—, —CSNH, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

$R^m$ and $R^k$ are independently hydrogen, halogen, $C_{1-6}$ alkyl, hydroxy, $C_{1-6}$ alkyloxy or nitro;

n is zero or one;

A is —NH(CH$_2$)$_m$—, —S—, —SO—, —SO$_2$—, —O—, —C≡C—, —CR$^8$R$^9$, —CR$^8$=CR$^9$—, phenyl, phenyl substituted by a $C_{1-6}$ alkyl, $C_{1-6}$ alkoxy, halogen, CO$_2$R$^8$, —(CH$_2$)$_m$OR$^8$, —(CH$_2$)$_m$NR$^9$R$^8$, or —COR$^{10}$ group, naphthyl, naphthyl substituted by a $C_{1-6}$ alkyl, $C_{1-6}$ alkoxy, halogen, CO$_2$R$^8$, —(CH$_2$)$_m$OR$^8$, —(CH$_2$)$_m$NR$^8$R$^9$ or —COR$^{10}$, or heteroaryl;

Q is phenyl, naphthyl or heteroaryl, said phenyl, naphthyl or heteroaryl group being optionally substituted by one to three same or different $C_{1-6}$ alkyl, $C_{1-6}$ fluoroalkyl, $C_{1-6}$ alkoxy, halogen, CO$_2$R$_{11}$, —(CH$_2$)$_q$OR$^{11}$, —(CH$_2$)$_q$NR$^{11}$R$^{12}$, —NHCOR$^{13}$ or —COR$^{13}$ with the proviso that when A is —S—, —SO—, —SO$_2$— or —O—, then Q is a phenyl, naphthyl or heteroaryl group substituted by one to three halogen, $C_{1-6}$ fluoroalkyl, CO$_2$R$^{11}$, —(CH$_2$)$_q$OR$^{11}$, —(CH$_2$)$_q$NR$^{11}$R$^{12}$, —NHCOR$^{13}$ or —COR$^{13}$;

$R^5$ and $R^6$ are each independently hydrogen or $C_{1-6}$ alkyl;

$R^8$ and $R^9$ are each independently hydrogen or $C_{1-6}$ alkyl;

$R^{10}$ and $R^{13}$ are each independently hydrogen, $C_{1-6}$ alkyl or $C_{1-6}$ fluoroalkyl;

$R^{11}$ and $R^{12}$ are each independently hydrogen or $C_{1-6}$ alkyl;

$R^a$ and $R^b$ are independently hydrogen or $C_{1-6}$ alkyl; but when n is one, $R^a$ and $R^b$ together can form a radical of the formula

Z is hydrogen, $C_{1-6}$ alkyl, benzyl, p-methoxybenzyl, allyl or trimethylsilylethyl;

m and q are independently 0 to 2;

p is 0 or 1 with the proviso that when p is 0 then Q is phenyl, naphthyl or heteroaryl substituted by one to three —(CH$_2$)$_q$OR$^{11}$, —(CH$_2$)$_q$NR$^{11}$R$^{12}$, or —COR$^{13}$ $R^2$ and $R^3$ are each independently hydrogen or $C_{1-6}$ alkyl;

$R^1$ is —CO$_2$Z, $C_{1-6}$ alkyl, —CH$_2$OH, —CONHR$^7$ or CHO;

$R^7$ is hydrogen or $C_{1-6}$ alkyl;

provided that when X is —C≡C—, A is not —CR$^8$=CR$^9$— or —C≡C—.

The new retinoid antagonists of formula II are useful as anti-inflammatory agents for treatment of chronic skin inflammatory diseases such as psoriasis and atopic dermatitis, as agents for the treatment of rheumatic diseases such as rheumatoid arthritis, as antitumor agents for the treatment of various tumors as well as non-malignant proliferative skin diseases, and as agents for the minimization or prevention of post-surgical adhesion formation.

DETAILED DESCRIPTION OF THE INVENTION

Figure 1:
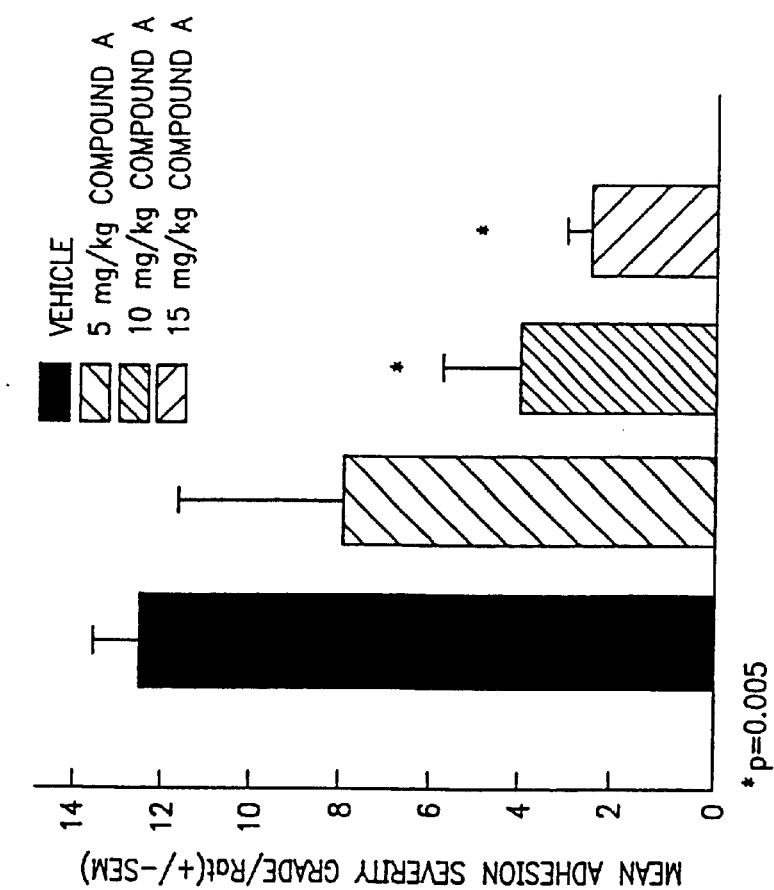
FIG. 1 shows the number and severity of caecal adhesions in rat after oral administration of a preferred retinoid antagonist of the present invention.
Figure 1:
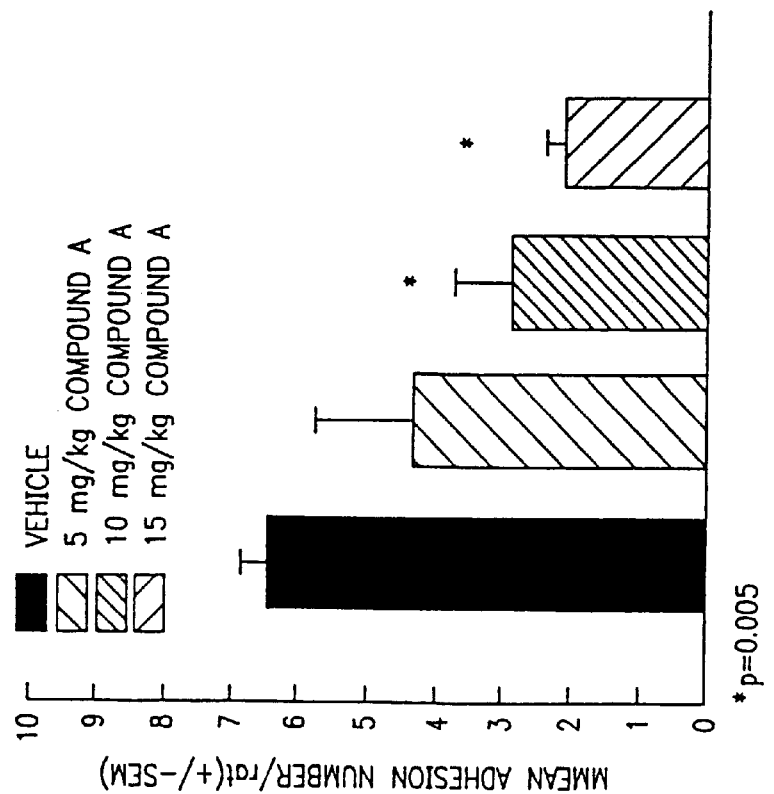

Adhesion formation, particularly following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction. In addition, adhesions are associated with chronic or recurrent pelvic pain and infertility in females.

Various approaches for the prevention of adhesion formation have been explored, but an effective therapeutic approach has not been discovered to date.

The use of retinoids for prevention of adhesion formation is described in U.S. Pat. No. 5,534,261. While the term "retinoid" as used in this patent is defined in several ways, it appears that the inventors intended this term to refer to retinoid agonists, as the specific embodiments and preferred compounds are all of this class. No mention is made of retinoid antagonists or whether such antagonists would have this desirable property.

The present inventors have unexpectedly found that retinoid antagonists possess utility to prevent or minimize adhesion formation and, in fact, appear to be significantly more effective for this use than retinoid agonists. Moreover, the retinoid antagonists are less toxic than retinoid agonists in that, unlike the agonists, they do not appear to induce hypervitaminois A, a syndrome which can result in death.

Thus, in one aspect, the present invention provides a method for the minimization or prevention of post-surgical adhesion formation between organ surfaces comprising administering an effective amount of a retinoid antagonist for a period of time sufficient to permit tissue repair.

In its broadest aspect, any retinoid antagonist as defined herein can be employed. The literature provides several examples of suitable retinoid antagonists. For example, retinoid antagonists are described in *journal of the Pharmaceutical Society of Japan*, Vol. 114, Issue 11, pages 847–862 (1994), in *Proc. Natl. Acad. Sci. USA*, Vol. 91, Issue 12, pages 5632–5636 (1994), in *J. Biol. Chem.*, Vol. 271, Issue 21, pages 12209–12212 (1996), in *J. Med. Chem.*, Vol. 38, pages 4764–4767 (1995), in *J. Med. Chem.*, Vol. 37, pages 1508–1517 (1994), in *Proc. Natl. Acad. Sci. USA*, Vol. 89, pages 7129–7133 (1992), in *Med. Chem. Res.*, Vol. 1, pages 220–225 (1991), in *J. Med. Chem.*, Vol. 38, pages 3163–3173 (1995), and in *J. Biol. Chem.*, Vol. 20, pages 11897–11903 (1996). Other retinoid antagonists can be found by using the assay procedures described below. Applicants believe that prior to their invention, no retinoid antagonists have been disclosed as having a therapeutic utility.

As noted above, the term "retinoid antagonist" as used herein means a compound which binds to all three of the retinoic acid receptor subtypes RARα, RARβ and RARγ but does not activate at least two of the three RAR receptor subtypes in a standard retinoid transactivation assay. Suitable binding and transactivation assays are disclosed in *Proc. Natl. Acad. Sci. USA*, Vol. 92, pg. 1812–1816, 1995. Functional antagonism is also illustrated in, for example, *J. Med. Chem.*, 38, 4764–4767 (1995), where the transactivation activity of retinoic acid is inhibited by increasing concentrations of the antagonist.

A preferred embodiment of the present invention is the use in the above method of a retinoid antagonist having the general formula

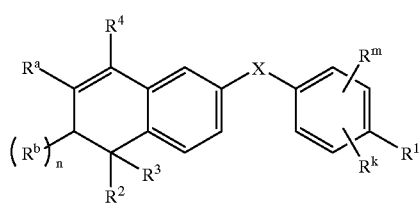

IA or a nontoxic pharmaceutically acceptable salt, physiologically hydrolyzable ester or solvate thereof, in which X is —O—CO—, —NH—CO—, —CS—NH, —CO—O—, —CO—NH—, —COS—, —SCO—, —SCH$_2$—, —CH$_2$—CH$_2$—, —C≡C, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$ alkyl, hydroxy, C$_{1-6}$alkyloxy or nitro;

n is zero or one;

R$^4$ is —(CH$_2$)$_t$—Y;

R$^1$ is —CO$_2$Z, —C$_{1-6}$ alkyl, CH$_2$OH, —CONHR$^y$ or CHO;

R$^2$ and R$^3$ are independently hydrogen or C$_{1-6}$ alkyl;

R$^a$ and R$^b$ are independently hydrogen or C$_{1-6}$ alkyl; but when n is one, R$^a$ and R$^b$ together can form a radical of the formula

Y is phenyl or naphthyl and both radicals can be optionally substituted with one to three same or different C$_{1-6}$ alkyl or halogen groups;

Z is hydrogen or C$_{1-6}$ alkyl;

R$^5$, R$^6$ and R$^y$ are independently hydrogen or C$_{1-6}$ alkyl; and t is zero to six.

In the present application, the numbers in subscript after the symbol "C" define the number of carbon atoms a particular group can contain. For example, C$_{1-6}$alkyl refers to straight and branched chain alkyl groups with one to six carbon atoms. For example, methyl, ethyl, n-propyl, isopropyl, n-butyl, t-butyl, n-pentyl, n-hexyl, 3-methylpentyl, etc. and C$_{3-6}$ cycloalkyl refers to cyclopropyl, cyclobutyl, cyclopentyl or cyclohexyl. The term "halogen" refers to fluorine, chlorine, bromine or iodine.

Some compounds of formula IA may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such a triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

When a compound of formula IA contains a carboxy group, it can form physiologically hydrolyzable esters which serve as prodrugs by being hydrolyzed in the body to yield formula IA compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula IA include C$_{1-6}$alkyl, benzyl, 4-methoxybenzyl, indanyl, phthalidyl, methoxymethyl, C$_{1-6}$alkanoyloxy, C$_{1-6}$alkyl, e.g. acetoxymethyl, pivaloyloxymethyl or propionyloxymethyl, C$_{1-6}$alkoxycarbonyloxy, C$_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephalosporin arts. Such esters are prepared by conventional techniques known in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The term "organ surface" is intended to encompass any internal organ of a living animal including but not limited to the uterus, intestines, liver, kidneys, heart and lungs.

The method of the present invention is applicable to all living animals. The preferred "subject" for the application of the invention is, however, a mammal. The most preferred subjects are humans.

A preferred embodiment of the present invention comprises the above-described method of preventing surgical adhesions wherein the retinoid antagonist is a compound of the formula

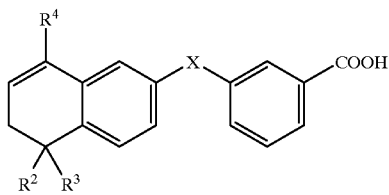

in which $R^2$ and $R^3$ are each independently $C_{1-6}$ alkyl, X is —$CR^5$=$CR^6$— in which $R^5$ and $R^6$ are each independently hydrogen or $C_{1-6}$ alkyl, and $R^4$ is —$(CH_2)_t$—Y in which t is 0 and Y is phenyl, phenyl substituted by 1–3 same or different halogen or $C_1$–$C_6$ alkyl substituents, or naphthyl.

In another aspect the present invention provides a new series of retinoid antagonist compounds of the formula

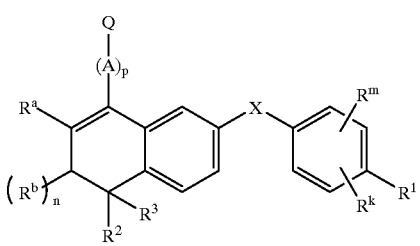

II or nontoxic pharmaceutically acceptable salts, physiologically hydrolyzable esters or solvates thereof, in which X is —O—CO—, —NH—CO—, —CSNH, —CO—O—, —CO—NH—, —COS—, —SCO—, —$SCH_2$—, —$CH_2$—$CH_2$—, —C≡C—, —$CH_2$—NH—, —$COCH_2$—, —NHCS—, —$CH_2S$—, —$CH_2O$—, —$OCH_2$—, —$NHCH_2$— or —$CR^5$=$CR^6$—;

$R^m$ and $R^k$ are independently hydrogen, halogen, $C_{1-6}$ alkyl, hydroxy, $C_{1-6}$ alkyloxy or nitro;

n is zero or one;

A is —$NH(CH_2)_m$—, —S—, —SO—, —$SO_2$—, —O—, —C≡C—, —$CR^8R^9$—, —$CR^8$=$CR^9$—, phenyl, phenyl substituted by a $C_{1-6}$ alkyl, $C_{1-6}$ alkoxy, halogen, $CO_2R^8$, —$(CH_2)_mOR^8$, —$(CH_2)_mNR^9R^8$, or —$COR^{10}$ group, naphthyl, naphthyl substituted by a $C_{1-6}$ alkyl, $C_{1-6}$ alkoxy, halogen, $CO_2R^8$, —$(CH_2)_mOR^8$, —$(CH_2)_mNR^8R^9$ or —$COR^{10}$, or heteroaryl;

Q is phenyl, naphthyl or heteroaryl, said phenyl, naphthyl or heteroaryl group being optionally substituted by one to three same or different $C_{1-6}$ alkyl, $C_{1-6}$ fluoroalkyl, $C_{1-6}$ alkoxy, halogen, $CO_2R^{11}$, —$(CH_2)_qOR^{11}$, —$(CH_2)_qNR^{11}R^{12}$, —$NHCOR^{13}$ or —$COR^{13}$ with the proviso that when A is —S—, —SO—, —$SO_2$— or —O—, then Q is a phenyl, naphthyl or heteroaryl group substituted by one to three halogen, $C_{1-6}$ fluoroalkyl, $CO_2R^{11}$, —$(CH_2)_qOR^{11}$, —$(CH_2)_qNR^{11}R^{12}$, —$NHCOR^{13}$ or —$COR^{13}$;

$R^5$ and $R^6$ are each independently hydrogen or $C_{1-6}$ alkyl;

$R^8$ and $R^9$ are each independently hydrogen or $C_{1-6}$ alkyl;

$R^{10}$ and $R^{13}$ are each independently hydrogen, $C_{1-6}$ alkyl or $C_{1-6}$ fluoroalkyl;

$R^{11}$ and $R^{12}$ are each independently hydrogen or $C_{1-6}$ alkyl;

$R^a$ and $R^b$ are independently hydrogen or $C_{1-6}$ alkyl; but when n is one, $R^a$ and $R^b$ together can form a radical of the formula

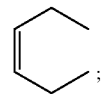

Z is hydrogen, $C_{1-6}$ alkyl, benzyl, p-methoxybenzyl, allyl or trimethylsilylethyl;

m and q are independently 0 to 2;

p is 0 or 1 with the proviso that when p is 0 then Q is phenyl, naphthyl or heteroaryl substituted by one to three —$(CH_2)_qOR^{11}$, —$(CH_2)_qNR^{11}R^{12}$, or —$COR^{13}$ $R^2$ and $R^3$ are each independently hydrogen or $C_{1-6}$ alkyl;

$R^1$ is —$CO_2Z$, $C_{1-6}$ alkyl, —$CH_2OH$, —$CONHR^7$ or CHO;

$R^1$ is hydrogen or $C_{1-6}$ alkyl;

provided that when X is —C≡C—, A is not —$CR^8$=$CR^9$— or —C≡C—.

The meanings of the substituent groups for the formula II compounds as well as the meanings for the terms "pharmaceutically acceptable salts and physiologically hydrolyzable esters" are, unless otherwise stated, the same as those described above for the formula IA compounds. The term "heteroaryl" as used herein includes mono-, bi- and polycyclic aromatic heterocyclic groups containing 1–4 O, N or S atoms; preferred are 5- and 6-membered heterocyclic groups such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc. and fused 5,6-membered and 6,6-membered aromatic heterocyclic groups such as benzofuranyl, isobenzofuranyl, benzothienyl, indolyl, isoindolyl, indazolyl, indolizinyl, isoquinolyl, quinolyl, naphthyridinyl, quinoxalinyl, quinazolinyl, pteridinyl etc.

The retinoid antagonists of general formula IA may be made by the procedures disclosed in co-pending U.S. Pat. No. 5,618,839 and in EP 661,259 A1 published Jul. 5, 1995.

The retinoid antagonists of general formula II may be made by known procedures. Suitable reaction schemes for preparing the formula II compounds are illustrated below.

As used herein and in the reaction schemes, the term "enol triflate or silyl formation" is intended to include conventional and well-known enolate formation procedures and subsequent trapping of this enolate by the well-known triflating or silylating agents. Thus the ketones are treated with an organic base such as 2,6-di-tert-butyl-4-methyl-pyridine, sodium hydride, potassium hydride, lithium diisopropylamide or lithium bis(trimethylsilyl)amide in an inert organic solvent such as tetrahydrofuran, dimethylformamide or dichloromethane and the like. The resulting enolates are then treated with triflic anhydride or 2-[N,N-bis(trifluoromethylsulfonyl)amino]pyridine and the like or an alkylsilyl chloride.

As used herein and in the reaction schemes, the term "Stille, Negishi or Suzuki-type coupling" is intended to include all the known cross-coupling methods that involve the reaction of an enol triflate with a tin, zinc, magnesium or boronic derivative catalyzed with a palladium(0) or paladium(II) catalyst such as tetrakistriphenylphosphinepalladium(0), bistriphenylphosphinepalladium(II) chloride, palladium(II) acetate, palladiumtris(dibenzylidene-acetone)di-palladium (0), bis(diphenylphosphineferrocene)palladium(II) chloride and the like or a nickel(0) or nickel(II) catalyst such as tetrakistriphenylphosphine-nickel(0), bistriphenylphosphinenickel(II) chloride and the like. Very often, as known by those skilled in the art, copper iodide, lithium chloride, zinc chloride or triphenylarsine, tris(2-furyl)phosphine or tri(2,4,6-trimethoxy-phenyl)phosphine must be added. These reactions are performed in an inert organic solvent such as dioxane, N-methylpyrrolidone, dimethylformamide, dimethoxyethane, tetrahydrofuran, toluene, benzene and the like.

As used herein and in the reaction schemes, the term "Heck coupling" is intended to include all known vinylations of alkenes or alkynes. Thus, a vinyl triflate reacts with various substituted or non-substituted alkenes or alkynes in the presence of a trialkylamine base or an inorganic base such as potassium carbonate, sodium acetate and the like and a catalytic amount of Pd(II) complex such as palladium(II) acetate, bistriphenylphosphinepalladium(II) chloride or bisacetonitrilepalladium(II) chloride. Sometimes a phosphine ligand may facilitate the reaction such as triphenylphosphine, tritolylphosphine, diphenylphosphine-ferrocene or diphenylphosphinepropane and the like.

As used herein and in the reaction schemes the term "hydrolysis" is intended to include conventional hydrolysis procedures of esters well-known to those skilled in the art. For example, methyl or ethyl esters may be removed by the use of aqueous solutions of sodium or potassium alkoxides in tetrahydrofuran or ethanol. The hydrolysis of tert-butyl esters is carried out under acidic conditions such as 90% trifluoroacetic acid or 6N hydrochloric acid in solvents such as tetrahydrofuran or dichloromethane. Allyl esters may be removed by the use of a Pd(0) catalyst such as tetrakistriphenylphosphinepalladium(0) and a nucleophile such as sodium acetate, potassium or sodium 2-ethylhexanoate, pyrolidine or morpholine and the like in an organic solvent such as acetonitrile, tetrahydrofuran, dichloromethane and the like. Finally, silyl esters or ethyltrimethylsilyl esters may be cleaved by the use of tetrabutylammonium fluoride in tetrahydrofuran. The term "hydrolysis" is also intended to include conventional hydrolysis procedures of alcohol protecting groups. For example, the hydrolysis of a p-methoxybenzyl, methoxymethyl, methyl ethers and the like may be carried out under acidic conditions such as 90% trifluoroacetic acid, 3N hydrochloric acid, sulfuric acid or boron tribromide in solvents such as dichloromethane, tetrahydrofuran, acetic acid and the like. Furthermore, organosilyl blocking groups such as tert-butyldimethylsilyl and triethylsilyl may advantageously be removed by the use of tetrabutylammonium fluoride in tetrahydrofuran.

As used herein and in the reaction schemes the term "acylation" is intended to include conventional and well-known acylation procedures for the preparation of amides, esters or thioesters such as the use of leaving groups and activating groups in organic solvents such as tetrahydrofuran, dichloromethane or mixture of aqueous-organic solvents in the presence of a base such as triethylamine, pyridine, dimethylaminopyridine and the like.

As used herein and in the reaction schemes the term "reduction" is intended to include well-known reduction procedures for aromatic nitro compounds or carbon-carbon multiple bonds such as reducing metals, i.e., activated zinc, iron or tin in presence of an acid such as acetic acid, hydrogen and palladium or sodium borohydride in presence of a nickel(II) or cobalt(II) catalyst. The term "reduction" is also intended to include well-known reduction procedures for the ester groups such as aluminum or boron hydrides.

As used herein and in the reaction schemes, the term "reductive amination" is intended to include the well-known reaction of an amine with an aldehyde in acidic conditions or in presence of titaniumisopropoxide to give the Schiff base which is then reduced with sodium cyanoborohydride or sodium borohydride in ethanol.

As used herein and in the reaction schemes the term "alkylation" is intended to include conventional and well-known alkylation procedures. Thus, the desired hydroxy or thiol groups which are to be alkylated are treated in the presence of an organic or inorganic base such as sodium hydride, potassium hydride, lithium diisopropylamine or lithium bis(trimethylsilyl)amide in an inert organic solvent such as tetrahydrofuran, dimethylformamide, hexamethylphosphoramide, dimethylsulfoxide, N-methylpyrolidinone and the like with an alkylating agent such as an alkyl, allyl or benzyl halide, mesylate or tosylate. The term "alkylation" is also intended to include conventional procedures involving the formation of an alkyl ketone from a carboxylic acid by the use of various alkyllithium reagents followed by trimethylsilyl chloride in an inert organic solvent such as tetrahydrofuran, dimethylformamide, N-methylpyrolidinone and the like.

As used herein and in the reaction schemes the term "substitution" is intended to include well-known transformation procedures of an hydroxy group to an alkylsulfonate or arylsulfonate group such as methanesulfonate (mesylate), trifluoromethanesulfonate (triflate) and p-toluenesulfonate (tosylate). These well known procedures involve for example the use of alkylsulfonyl or arylsulfonyl chlorides or anhydrides in an organic solvent such as dichloromethane or tetrahydrofuran in the presence of a base such as triethylamine, pyridine, dimethylaminopyridine, 2,6-di-tert-butyl-4-methyl-pyridine and the like. The term "substitution" is also intended to include well-known conversion procedures of a hydroxy group to a halide group such as chloride, bromide or iodide by the use of carbon tetrachloride or carbon tetrabromide in the presence of triphenylphosphine, or sodium iodide in an organic solvent such as acetone, dimethylformamide and the like.

As used herein and in the reaction schemes, the term "Horner-Emmons reaction" is intended to include conventional methods of Horner-Emmons olefination reactions of aldehydes or ketones by the use of an alkyl or aryl phosphonate and a base such as sodium hydride, lithium diisopropylamide or lithium bis(trimethylsilyl)amide and the like in an inert organic solvent such as tetrahydrofuran, dichloromethane, benzene and the like.

Scheme 1
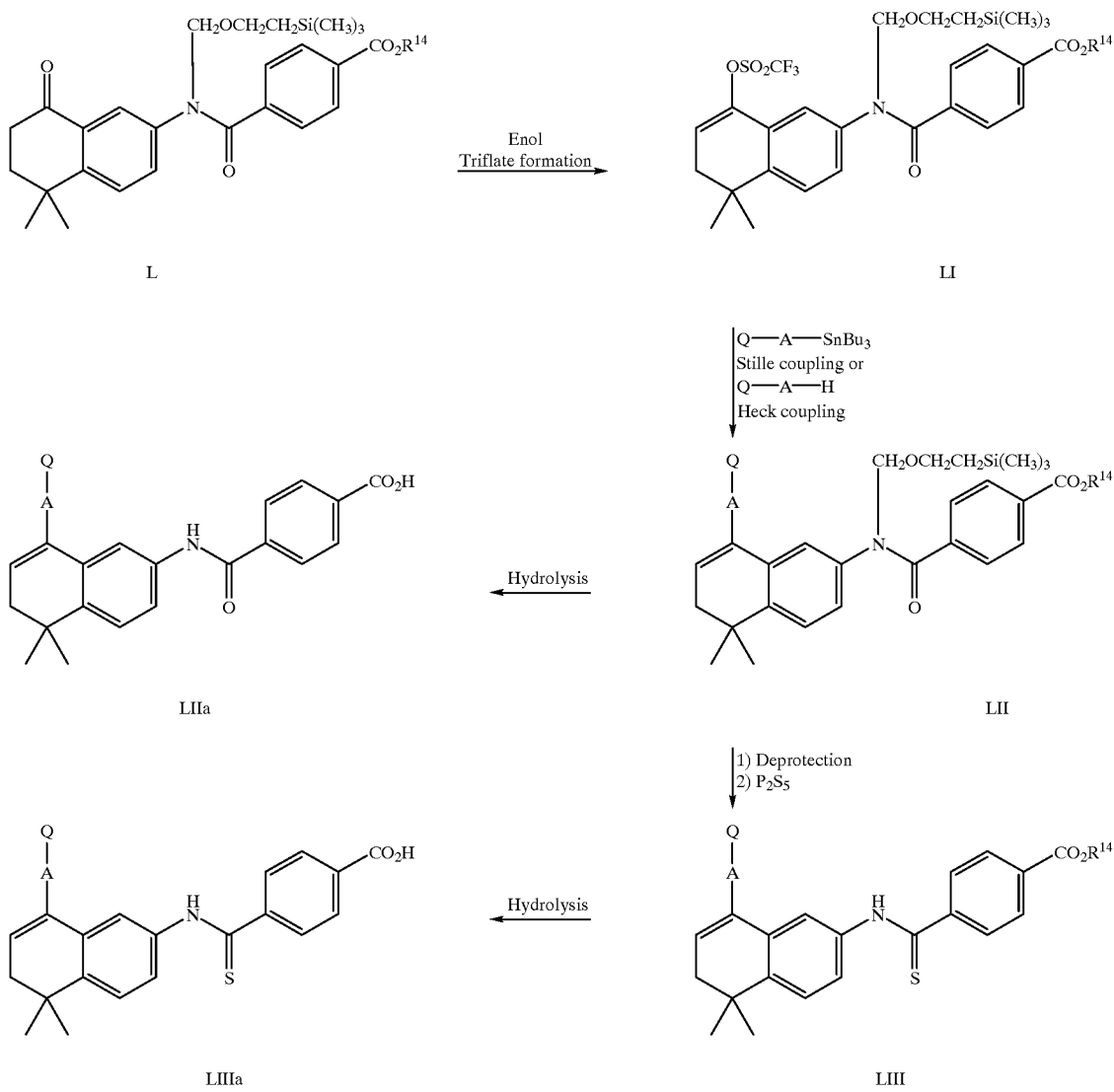
R[14] = carboxyl protecting group
Scheme 2
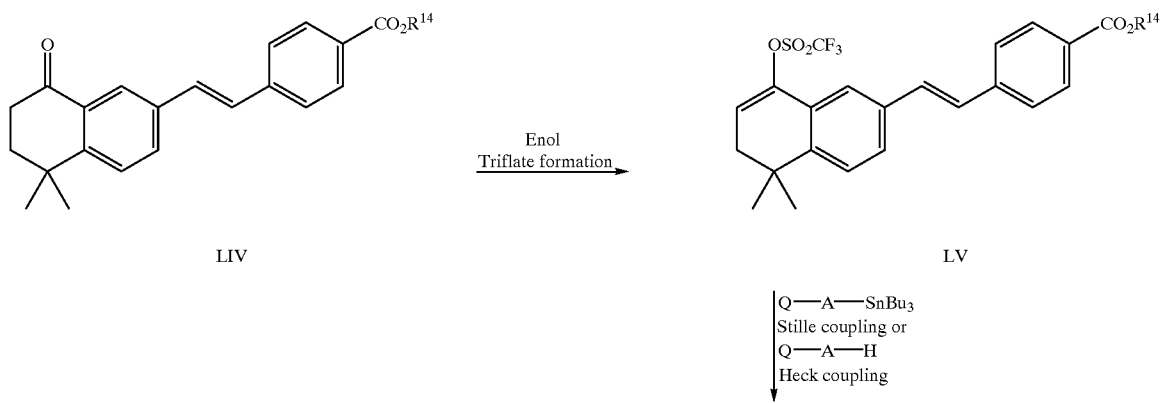

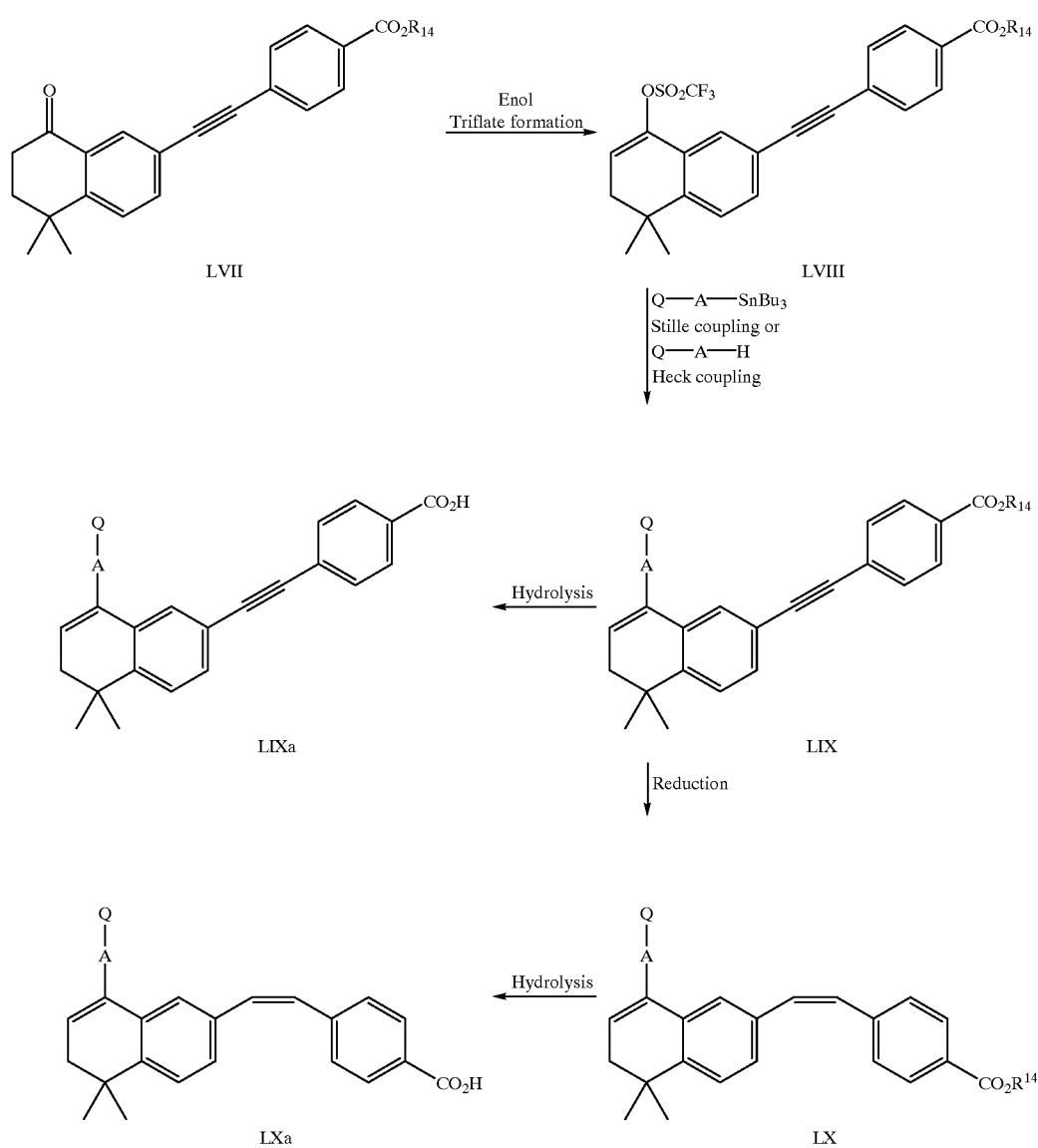
SCHEME 3

SCHEME 4
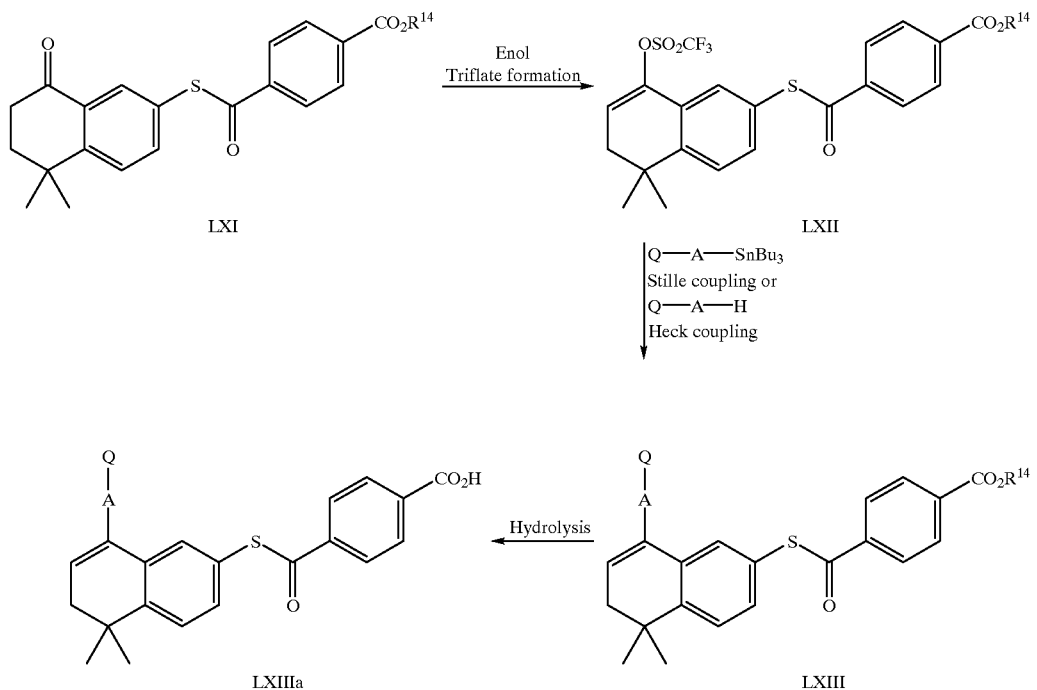
SCHEME 5
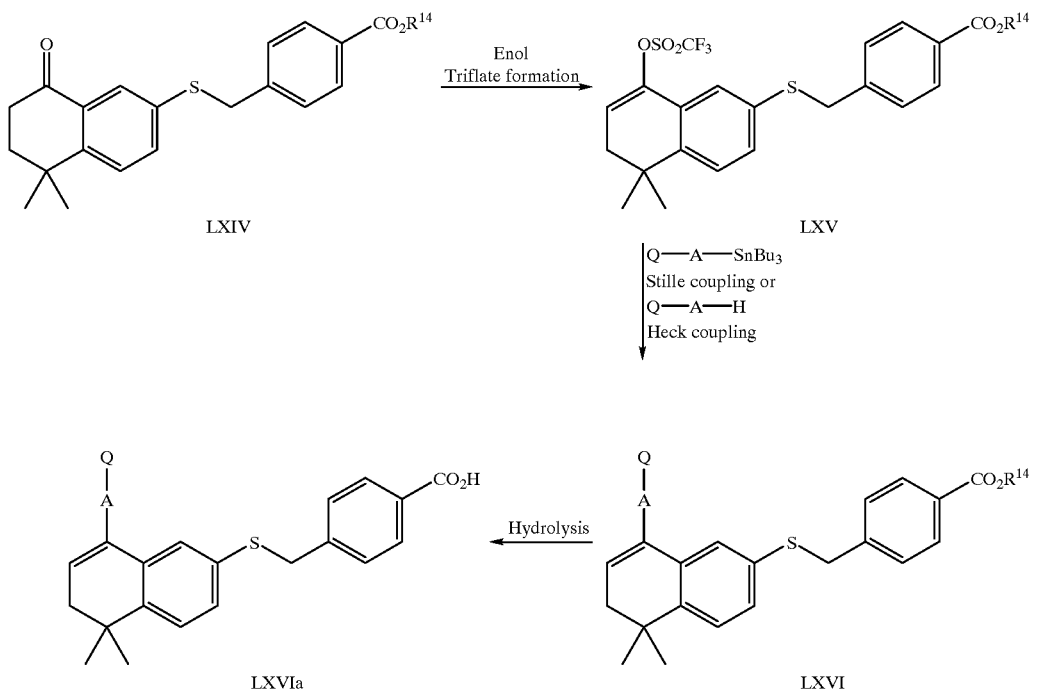

SCHEME 6
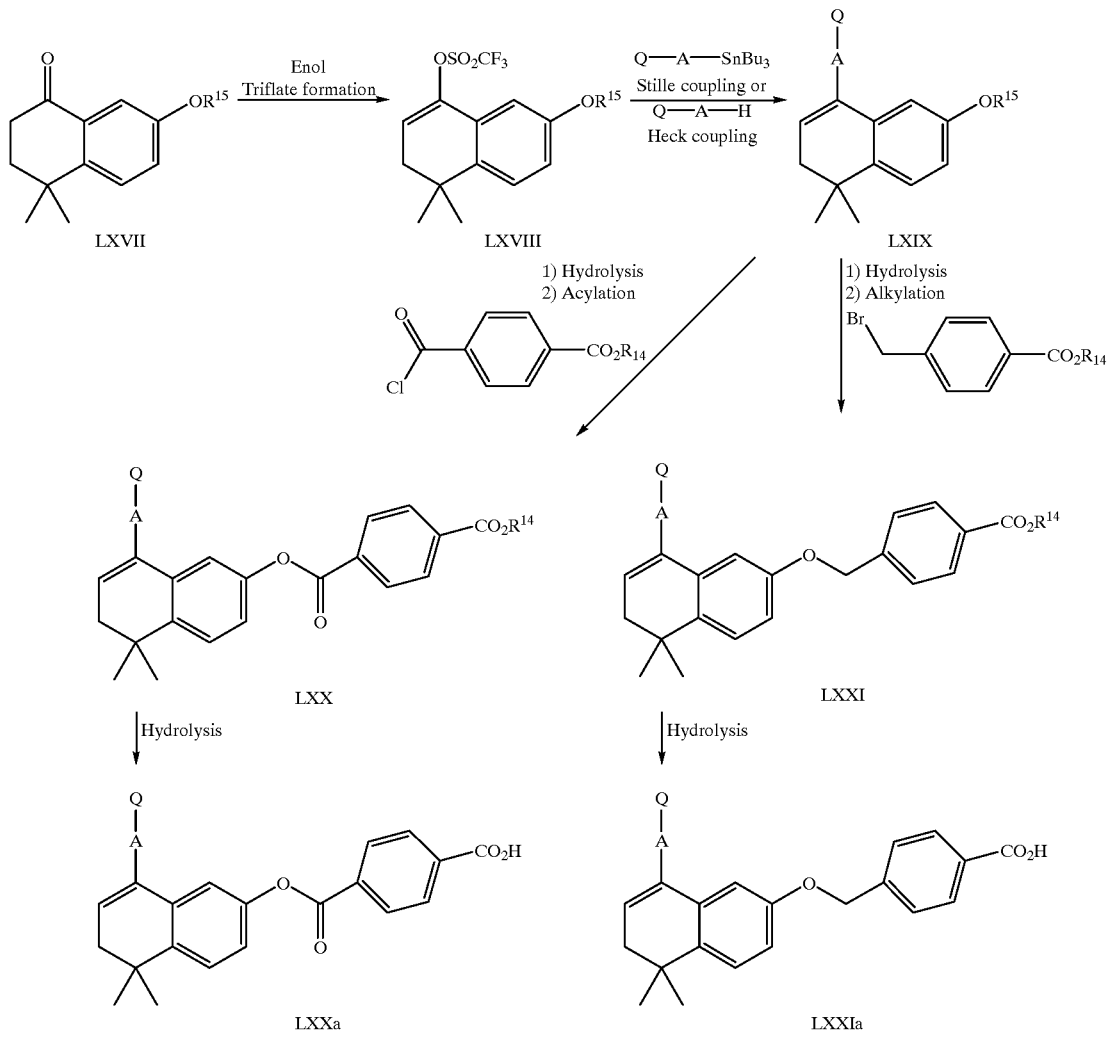
$R^{15}$ = ether protecting group
SCHEME 7
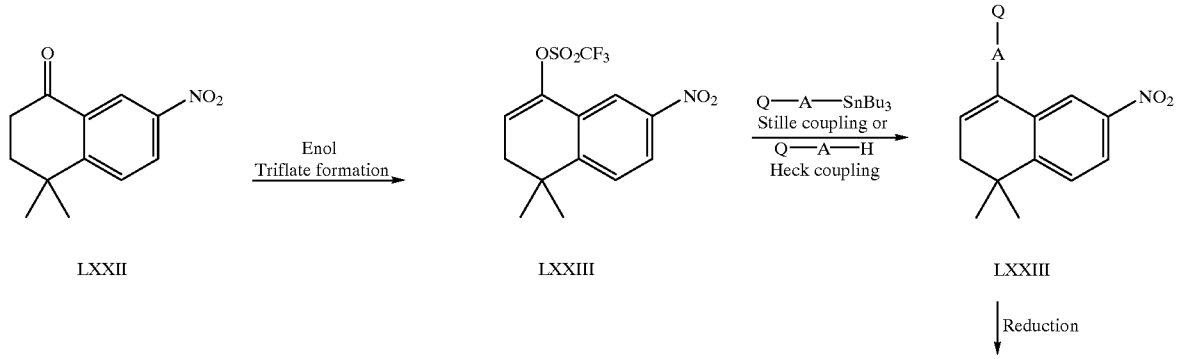

-continued
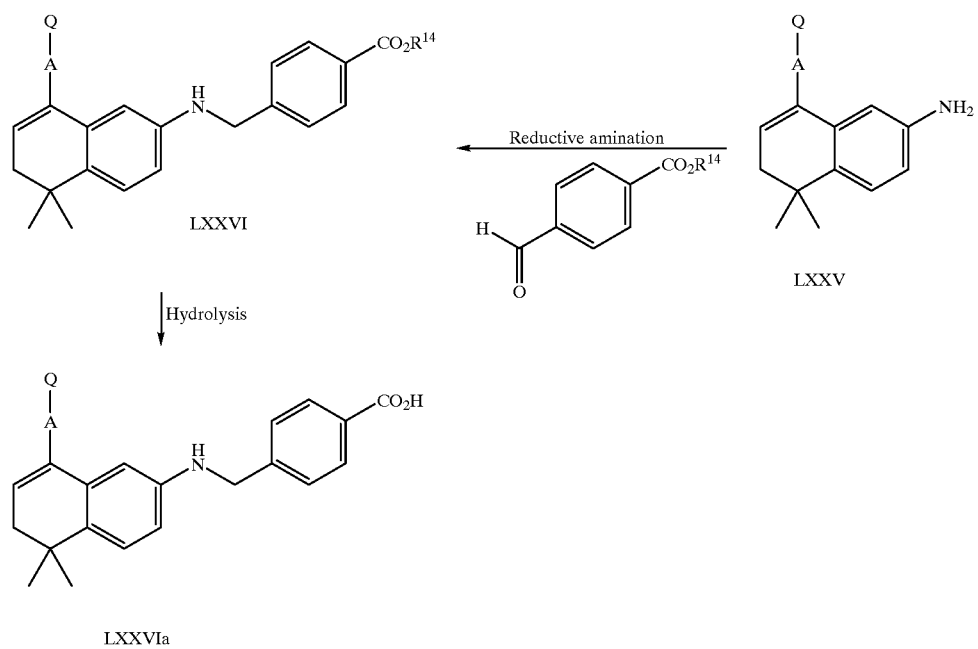
SCHEME 8
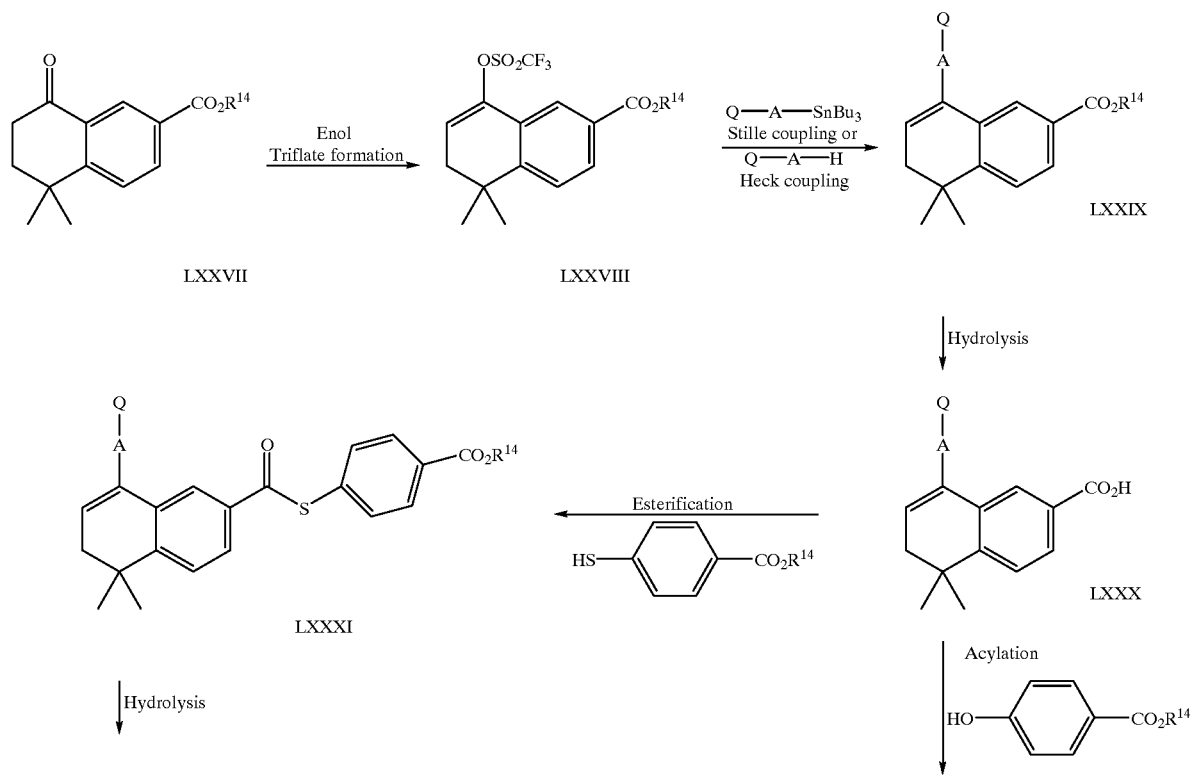

-continued
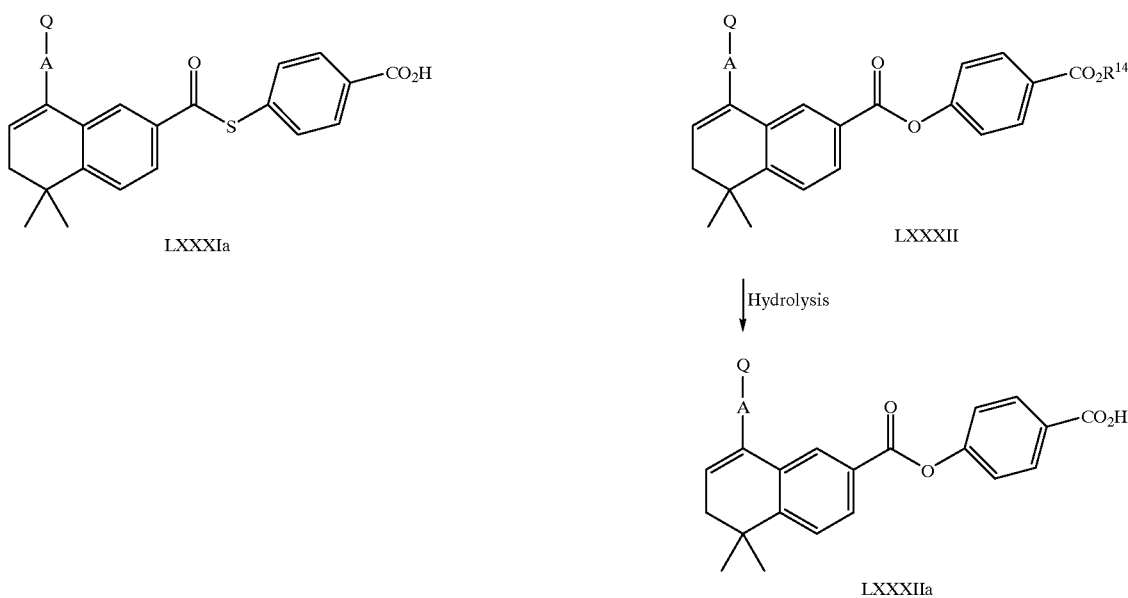
SCHEME 9
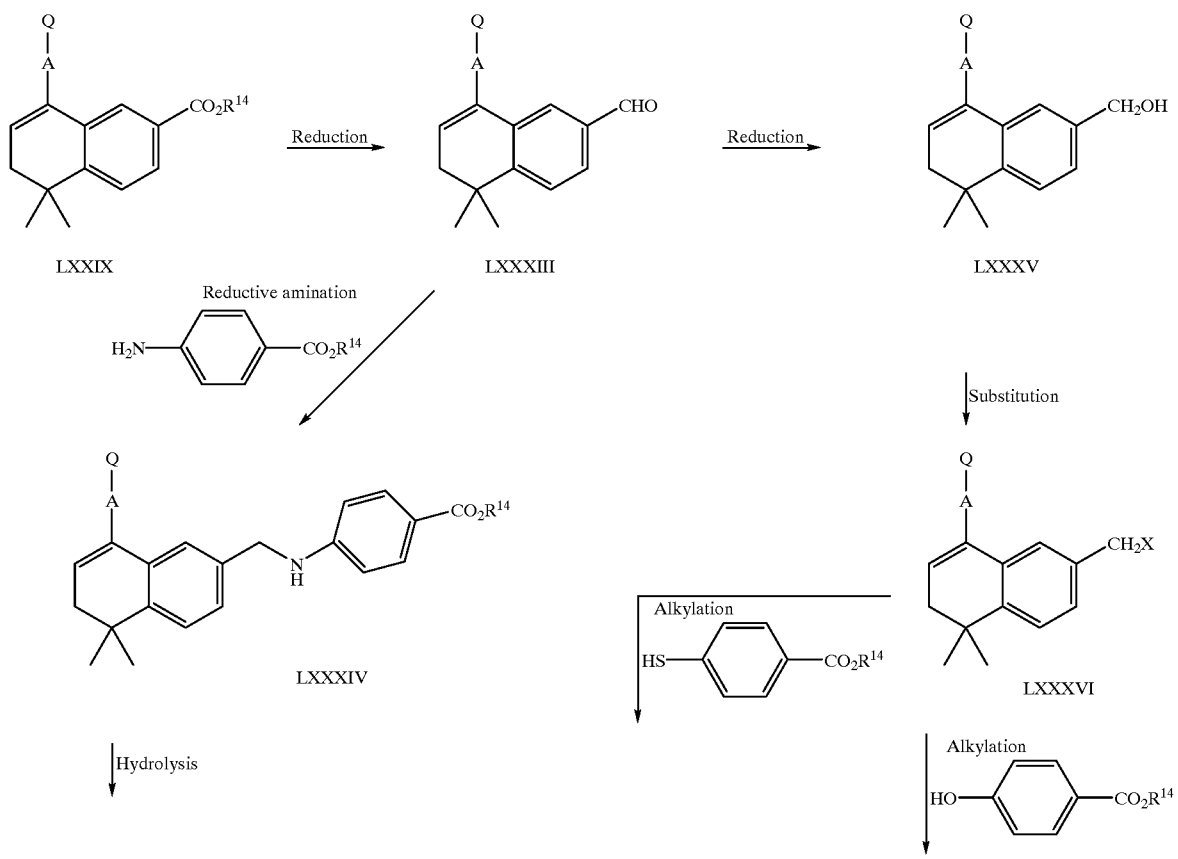

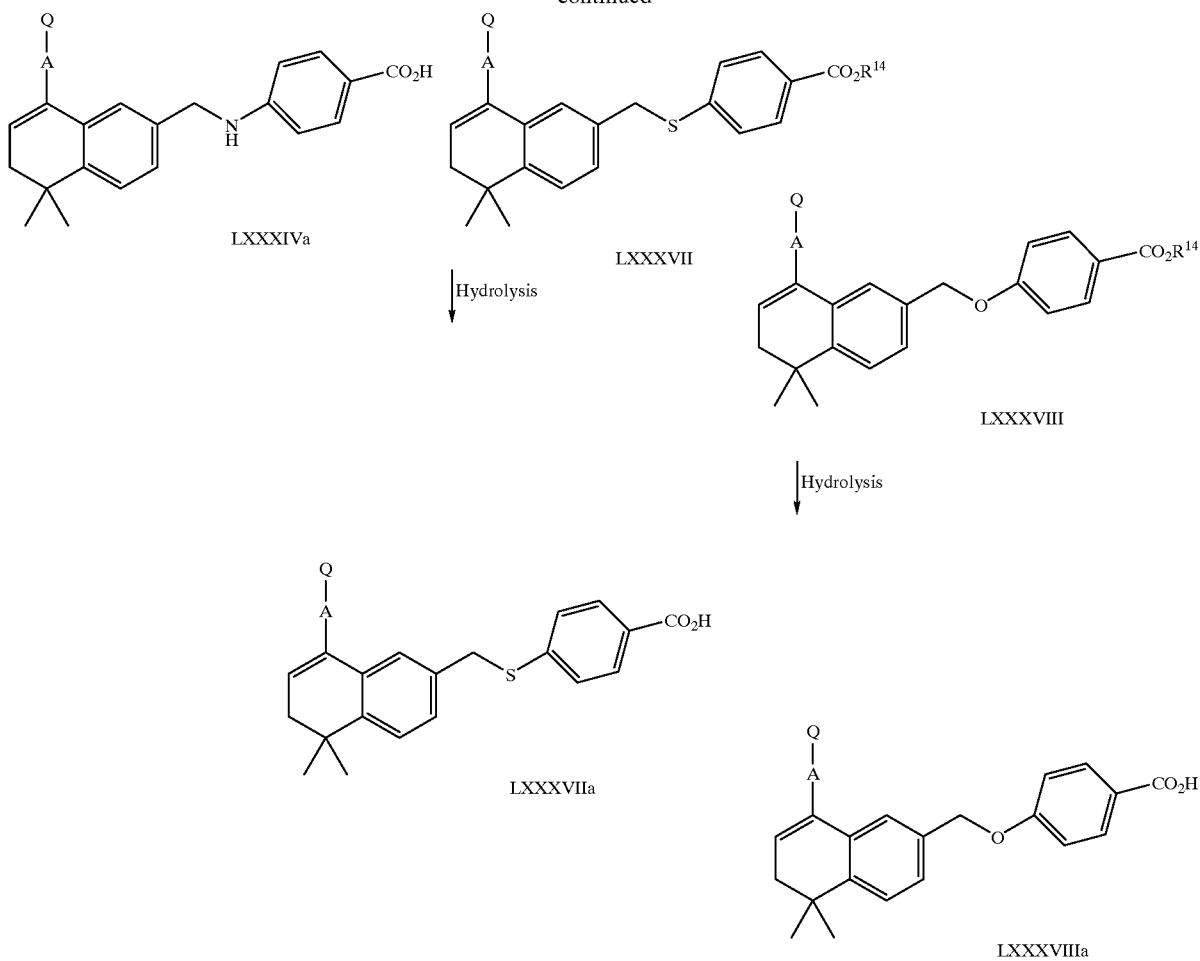
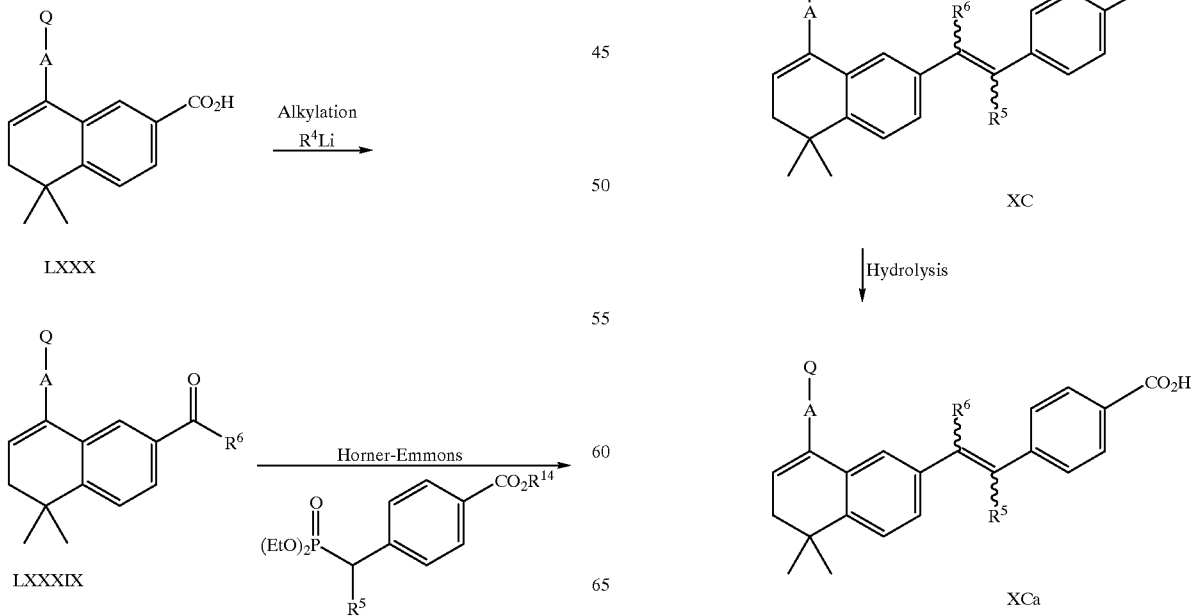

When R⁴ = Me
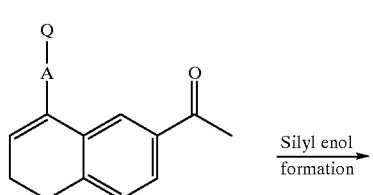
LXXXIX
Silyl enol formation →
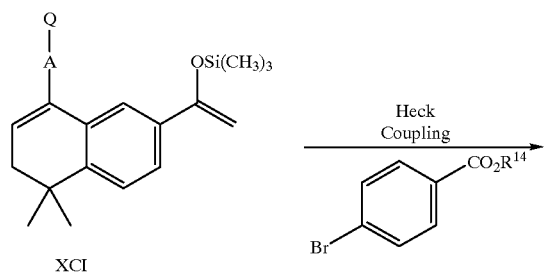
XCI
Heck Coupling →
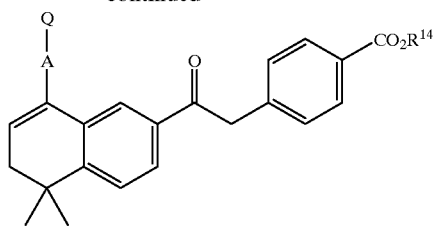
XCII
Hydrolysis ↓
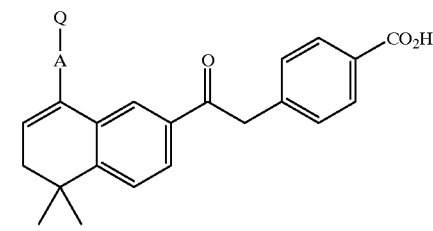
XCIIa
SCHEME 11
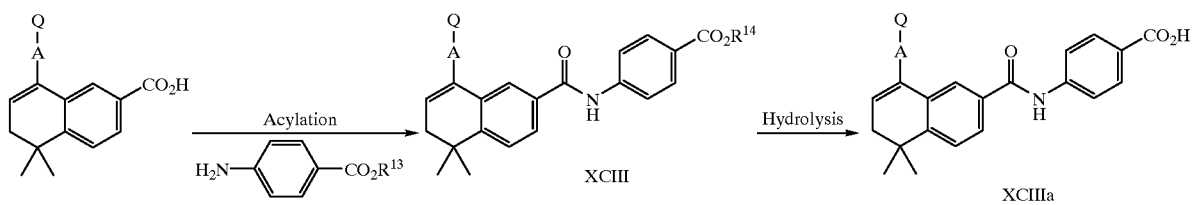
P₂S₅ ↓
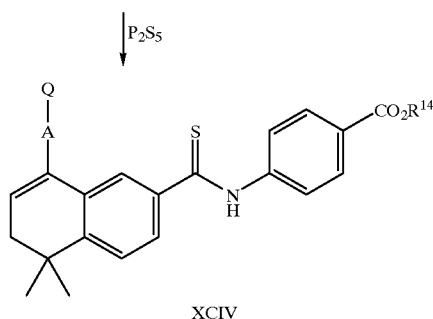
XCIV
Hydrolysis ↓
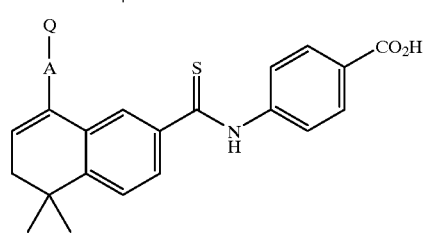
XCIVa

SCHEME 1–2
(II, where X=—NHCO—, —NHCS—, OR —CH=CH—)

Compound L (from European Patent application 661,259) is converted via base and a source of $CF_3SO_2$— (as, for example, trifluoromethanesulfonic anhydride or 2-(N,N-di(trifluoromethanesulfonamido)pyridine) into the corresponding trifluoromethanesulfonate ("triflate") LI, to which the side chain is then appended via, for example, Stille-type or Heck-type coupling to give protected ester LII. The protecting groups can then be cleaved off using procedures known in the art to give LIIa (II, X=NHCO). Alternatively, LII can be converted via deprotection of the amide nitrogen atom via F treatment followed by conversion of the amide carbonyl to the thiocarbonyl using $P_2S_5$ into thioamide LII. The carboxylate ester can then be hydrolyzed under standard conditions to give final compound LIIIa (II, X=NHCS). In a similar manner, (SCHEME 2) LIV (from European Patent application 661,259) can be converted to its corresponding triflate LV. The side chain can be installed as described to give LVI, which can be hydrolyzed to final product LVIa (II, X=trans-CH=CH).

SCHEME 3–4
(II, where X=C≡C, cis —CH=CH, or SCO)

Alkyne LVII (from European Patent application 661,259) can be converted to its vinyl triflate LVIII and the side chain can be appended as above to give LIX, which can be hydrolyzed directly under standard conditions to give LIXa (II, X=C≡C) or hydrogenated using a weakly active catalyst (for example, $Pd/BaSO_4$) to give LX, which can also be hydrolyzed under standard conditions to give LXa (II, X=cis-CH=CH). Similarly (SCHEME 4) (where protecting group $R^{14}$ is t-butyl), thioester LXI (from European Patent application 661,259) can be converted to vinyl triflate LXII, the side chain can be installed to give LXIII, and the carboxylate ester can be selectively hydrolyzed to give LXIIa. (II, X=SCO).

SCHEME 5
(II, where X=$SCH_2$)

Thioether LXIV (from European Patent application 661,259) is converted as above into vinyl triflate LXV and into LXVI from which final compound LXVIa (II, X=$SCH_2$) is obtained by hydrolysis.

SCHEME 6
(II, where X=OCO OR $OCH_2$)

Keto-ether LXVII (from European Patent application 661,259, where $R^{15}$ is a trialkyl silyl protecting group) is converted to vinyl triflate LXVIII as described above. The side chain is then installed as described above to give LXIX. Protecting group $R^{15}$ is then selectively removed and LXIX ($R^{15}$=H) is acylated with commercially available methyl p-chloroformyl benzoate to give LXX ($R^{14}$=$CH_3$) which is then hydrolyzed to give LXXa (II, X=OCO). Alternatively, the protecting group can be removed from LXIX and the freed hydroxyl alkylated with commercially available alkyl p(bromomethyl)benzoates to give LXXI, which can then be hydrolyzed to give LXXIa (II, X=$OCH_2$).

SCHEME 7
(II, where X=$NHCH_2$)

Nitrotetralone LXXII (from European Patent application 661,259) can be converted to vinyl triflate LXXIII, the side chain installed as described to give LXXIV, then the nitro group can be reduced to give amino compound LXXV. Reductive amination with commercially available alkyl p-formyl benzoates will give LXXVI, which can be hydrolyzed to give final compound LXXVIa (II, X=$NHCH_2$).

SCHEME 8
(II, where X=COS or COO)

Keto ester LXXVII (from European Patent application 661,259) is converted into its vinyl triflate LXXVIII and then to LXXIX as described. The ester is then hydrolyzed to give LXXX, which can be reacted with alkyl p-mercaptobenzoates to give LXXXI followed by hydrolysis to give LXXXIa (II, X=COS). Alternatively, LXXX can be reacted with alkyl p-hydroxybenzoates to give LXXXII, which can then be hydrolyzed to give LXXXIIa (II, X=COO).

SCHEME 9
(II, where X=$CH_2NH$, $CH_2S$, or $CH_2O$)

Ester LXXIX (from scheme 8) is reduced, using methods known in the art, to aldehyde LXXXIII. This can be reductively aminated using alkyl p-aminobenzoates to give LXXXIV, which can then be hydrolyzed to give LXXXIVa (II, X=$CH_2NH$). Alternatively, LXXXIII can be further reduced to alcohol LXXXV, which can be converted using standard methods to LXXXVI (where X=Br, for example, using triphenyl phosphine and $CBr_4$). LXXXVI can then be used to alkylate alkyl p-mercaptobenzoates to give LXXXVII which are then hydrolyzed to give LXXXVIIa (II, X=$CH_2S$) or alkylate alkyl p-hydroxybenzoates to give LXXXVIII, which can then be hydrolyzed to give LXXXVIIIa (II, X=$CH_2O$).

SCHEME 10
(II, where X=$CR^6$=$CR^5$ or $COCH_2$)

Acid LXXX (from scheme 8) is treated with an alkyl lithium to give LXXXIX, which is then reacted via the well-known Horner-Emmons reaction with a p-(carboalkoxy)benzyl phosphonate to give XC, which is hydrolyzed to give XCa (II, X=$CR^6$=$CR^5$). Intermediate ketone LXXXIX (where $R^6$=$CH_3$) can be converted with base and chlorotrimethylsilane into silyl enol XCI, which is then coupled under Heck conditions with commercially available alkyl p-bromobenzoates to give XCII, which can then be hydrolyzed to give XCIIa (II, X=$COCH_2$).

SCHEME 11
(II, where X=CONH or CSNH)

Acid LXXX (from scheme 8) can be coupled under standard conditions (for example, by conversion to its acid chloride and coupling directly or using the free acid plus a carbodiimide activating/dehydrating agent) with alkyl p-aminobenzoates to give XCIII, which can be directly hydrolyzed to give XCIIIa (II, X=CONH). Alternatively, XCIII can be treated with $P_2S_5$ to give thioamide XCIV, which can then be hydrolyzed to give XCIVa (II, X=CSNH).

DESCRIPTION OF SPECIFIC EMBODIMENTS

The specific examples which follow illustrate the synthesis of representative compounds of the present invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quarter (dq). The solvents employed for taking NMR spectra are DMSO-$d_6$ (perdeuterodi-methylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value. All melting points were determined on a Gallenkamp melting point apparatus and were not corrected. Analytical grade solvents were used for reactions and chromatographics. Flash column chromatographics were performed on Merck silica gel 60 (230–400 Mesh) and Merck silica gel 60 $F_{254}$ 0.5 mm plates were used.

CELITE is a registered trademark of the Johns-Manville Products Corporation for diatomaceous earth.

The abbreviations used herein are conventional abbreviations widely employed in the art.

EXAMPLE 1

4-[(E)-[5,6-Dihydro-5,5-dimethyl-8-[(E)-phenylethenyl]-2-naphthalenyl]-ethenyl]benzoic Acid Methyl 4-[(E)-[5,6-dihydro-5,5-dimethyl-8-trifluoromethanesulfonyloxy-2-naphthalenyl]ethenyl] benzoate A solution of methyl 4-[[(E)-(5,6,7,8-tetrahydro-5,5-dimethyl-8-oxo)-2-naphthalenyl]vinyl]benzoate (10.02 g, 30 mmol) in tetrahydrofuran (200 mL) at –78° C. was treated dropwise with a solution of lithium bis (trimethylsilyl)amide (1.0M in tetrahydrofuran, 42 mL, 42 mmol). The solution was stirred for 30 minutes then treated with a solution of 2-[N,N-bis(trifluoromethyl-sulfonyl) amino]pyridine (14 g, 39 mmol) in tetrahydrofuran (100 mL). The mixture was stirred overnight and was allowed to reach room temperature. The mixture was cooled down to 0–5° C., diluted with water (200 mL) and ethyl acetate (200 mL). The organic phase was separated and the aqueous phase was extracted with ethyl acetate (100 mL). The combined organic phases were washed with brine and dried over anhydrous magnesium sulfate, filtered and concentrated. The residue was purified by silica gel chromatography (toluene to toluene/ethyl acetate 8:2) and triturated in hexanes to give the title material (10.5 g, 75%) as a white solid.

$^1$H NMR 400 MHz ($CDCl_3$) δ (ppm): 1.34 (6H, s, 2× —$CH_3$), 2.45 (2H, d, J=4.8 Hz, H-6'), 3.94 (3H, s, —$OCH_3$), 6.02 (1H, t, J=4.8 Hz, H-7'), 7.13 (1H, d, J=16.3 Hz, vinyl H), 7.22 (1H, d, J=16.3 Hz, vinyl H), 7.34 (1H, d, J=8.0 Hz, H-4'), 7.51 (1H, dd, J=8.0 and 1.6 Hz, H-3'), 7.54 (1H, br s, H-1'), 7.59 (2H, d, J=8.3 Hz, H-3 and H-5), 8.05 (2H, d, J=8.4 Hz, H-2 and H-6).

Methyl 4-[(E)-[5,6-dihydro-5,5-dimethyl-8-[(E)-phenylethenyl]-2-naphthalenyl]ethenyl]benzoate A solution of methyl 4-[(E)-[5,6-dihydro-5,5-dimethyl-8-trifluoromethanesulfonyloxy-2-naphthalenyl]ethenyl] benzoate (0.300 g, 0.644 mmol) in dioxane (10 mL) was treated with (E)-β-styryltributyltin (0.507 g, 1.29 mmol), lithium chloride (0.082 g, 1.931 mmol) and tetrakis (triphenylphosphine)-palladium(0) (0.037 g, 0.032 mmol). The solution was degassed, then heated to 95° C. for ≈8 hours. After dilution with dichloromethane, the mixture was treated with ammonium hydroxide 10% and filtered through a celite pad. The aqueous phase was then separated and the organic layer was washed with brine, dried over anhydrous magnesium sulfate, filtered and concentrated. The residue was purified by silica gel chromatography (hexane/ethyl acetate 19:1 to 9:1) and the solid obtained (0.261 g, 96%) was recrystallized from dichloromethane/hexane to give the title material (0.228 g, 84%) as white crystals.

m.p.: 125° C. IR (KBr) $\upsilon_{max}$ ($cm^{-1}$): 2950, 1705 (C=O), 1600. $^1$H NMR 400 MHz ($CDCl_3$) δ (ppm): 1.33 (6H, s, 2× —$CH_3$), 2.34 (2H, d, J=4.5 Hz, H-6'), 3.93 (3H, s, —OMe), 6.28 (1H, t, J=4.6 Hz, H-7'), 6.94 (1H, d, J=16.0 Hz, vinyl H), 7.10 (1H, d, J=16.3 Hz, vinyl H), 7.11 (1H, d, J=16.0 Hz, vinyl H), 7.23 (1H, d, J=16.3 Hz, vinyl H), 7.29–7.58 (10H, 3 sets of m, H-phenyl, H-1', H-3', H-4', H-3 and H-5), 8.02 (2H, d, J=8.4 Hz, H-2 and H-6). Anal. Calcd. for $C_{30}H_{28}O_2$·0.5 $H_2O$: C 84.99; H 6.66; Found: C 84.78; H 6.65.

4-[(E)-[5,6-Dihydro-5,5-dimethyl-8-[(E)-phenylethenyl]-2-naphthalenyl]ethenyl]benzoic Acid To a stirred solution of methyl 4-[(E)-[5,6-dihydro-5,5-dimethyl-8-[(E)-phenylethenyl]-2-naphthalenyl]ethenyl] benzoate (0.206 g, 0.49 mmol) in a mixture of tetrahydrofuran/ethanol (1:1, 2 mL) was added aqueous sodium hydroxide (5N, 0.98 mL, 4.90 mmol). The mixture was stirred overnight. Hydrochloric acid 1N was then added to precipitate the acid and ≈half of the volume of the solvents was evaporated. The white solid was filtered and washed with water. The solid was then dissolved in dichloromethane/ethanol, filtered and recrystallized from this mixture by evaporating the solvents. The title compound was obtained (0.149 g, 75%) as a white solid.

IR (KBr) $\upsilon_{max}$ ($cm^{-1}$): 3200–1800 (br), 1675 (C=O), 1600. $^1$H NMR 400 MHz (DMSO-$d_6$) δ (ppm): 1.26 (6H, s, 2× —$CH_3$), 2.30 (2H, d, J=4.7 Hz, H-6'), 6.36 (1H, t, J=4.7 Hz, H-7'), 6.98 (1H, d, J=16.0 Hz, vinyl H), 7.26–7.41 and 7.63–7.65 (9H, 3 sets of m, H-phenyl, vinyl H, H-1' and H-4'), 7.46 (1H, d, J=16.5 Hz, vinyl H), 7.60 (1H, dd, J=8.1 and 1.5 Hz, H-3'), 7.72 (2H, d, J=8.4 Hz, H-3 and H-5), 7.91 (2H, d, J=8.4 Hz, H-2 and H-6). Anal. Calcd. for $C_{29}H_{26}O_2$: C 85.68; H 6.45; Found: C 85.46; H 6.28.

EXAMPLE 2

4-[(E)-(5,6-Dihydro-5,5-dimethyl-8-4-biphenylethynyl)-2-naphthalenyl)-ethenyl]benzoic Acid Methyl 4-[(E)-(5,6-dihydro-5,5-dimethyl-8-4-biphenylethynyl)-2-naphthalenyl)-ethenyl]benzoate A solution of methyl 4-[(E)-[5,6-dihydro-5,5-dimethyl-8-trifluoromethane-sulfonyloxy-2-naphthalenyl]ethenyl] benzoate (0.400 g, 0.86 mmol) in tetrahydrofuran (13 mL) was degassed and cooled down to 0–5° C. 4-Biphenylacetylene (0.382 mg, 2.15 mmol) was added in this solution, followed by bis(triphenylphosphine)palladium (II) chloride (26 mg), copper(I) iodide (26 mg) and diisopropylamine (2.1 mL). The mixture was stirred for 1 hour at 0–5° C. The resulting black solution was diluted in ethyl ether, washed with water, saturated bicarbonate and brine, dried over anhydrous magnesium sulfate, filtered and concentrated. The residue was purified by silica gel chromatography (ethyl acetate/toluene 0:100 to 100:0) and afforded the title compound (0.373 g, 88%) as a white solid after trituration in hexane.

IR (KBr) $\upsilon_{max}$ ($cm^{-1}$): 2950, 1715 (C=O), 1605. $^1$H NMR 400 MHz ($CDCl_3$) δ (ppm): 1.34 (6H, s, 2× —$CH_3$), 2.42 (2H, d, J=4.9 Hz, H-6'), 3.94 (3H, s, —$OCH_3$), 6.57 (1H, t, J=4.8 Hz, H-7'), 7.16 (1H, d, J=16.3 Hz, vinyl H), 7.28 (1H, d, J=16.3 Hz, vinyl H), 7.35–7.41, 7.46–7.50 and 7.63–7.69 (1H, 3 sets of m, H-3', H-4', H-biphenyl), 7.59 (2H, d, J=8.4 Hz, H-3 and H-5), 7.89 (1H, d, J=1.6 Hz, H-1'), 8.04 (2H, d, J=8.3 Hz, H-2 and H-6). Anal. Calcd. for $C_{36}H_{30}O_2$: C 87.42; H 6.11. Found: C 87.37, H 6.19.

4-[(E)-(5,6-Dihydro-5,5-dimethyl-8-4-biphenylethynyl)-2-naphthalenyl)-ethenyl]benzoic Acid A solution of methyl 4-[(E)-(5,6-dihydro-5,5-dimethyl-8-4-biphenylethynyl)-2-naphthalenyl)ethenyl]benzoate (0.373 g, 0.75 mmol) in tetrahydrofuran/ethanol (1:1, 12 mL) was treated with aqueous sodium hydroxide (10N, 0.75 mL) and the mixture was stirred for 18 hours at room temperature. Hydrochloric acid 1N (30 mL) was then added to precipitate the acid and the white precipitate was allowed to rest at 5° C. for 1 hour. The precipitate was filtered and washed with water. The solid was then dissolved in dichloromethane/ethanol (1:1), filtered and recrystallized from this mixture by slowly evaporating the solvents. The title compound was obtained (0.290 g, 80%) as a white solid.

IR (KBr) $\upsilon_{max}$ (cm$^{-1}$): 3650–2700 (br), 2960, 1685 (C=O), 1605. $^1$H NMR 400 MHz (DMSO-d$_6$) δ (ppm): 1.38 (6H, s, 2× —CH$_3$), 2.40 (2H, d, J=4.8 Hz, H-6'), 6.62 (1H, t, J=4.8 Hz, H-7'), 7.30 (1H, d, J=16.4 Hz, vinyl H), 7.41–7.44, 7.48–7.54 and 7.75–7.79 (13H, 3 sets of m, vinyl H, H-3, H-5, H-4', H-biphenyl), 7.67 (1H, br d, J=8.1 Hz, H-3'), 7.30 (1H, d, J=1.5 Hz, H-1'), 7.93 (2H, d, J=8.3 Hz, H-2 and H-6). Anal. Calcd. for $C_{35}H_{28}O_2$: C 87.47; H 5.87. Found: C 87.38; H 5.92.

EXAMPLE 3

4-[(E)-[5,6-Dihydro-5,5-dimethyl-8-4-biphenyl)-2-naphthalenyl]ethenyl]benzoic Acid The title material was prepared by the procedure described in Example 1 in using 4-biphenyltrimethyltin. Methyl 4-[(E)-[5,6-dihydro-5,5-dimethyl-8-4-biphenyl)-2-naphthalenyl]ethenyl]benzoate IR (KBr) $\upsilon_{max}$ (cm$^{-1}$): 3010, 2950, 1710 (C=O), 1600. $^1$H NMR 400 MHz (CDCl$_3$) δ (ppm): 1.37 (6H, s, 2× —CH$_3$), 2.40 (2H, d, J=4.7 Hz, H-6'), 3.92 (3H, s, —OCH$_3$), 6.1 (1H, t, J=4.7 Hz, H-7'), 6.98 (1H, d, J=16.3 Hz, vinyl-H), 7.13 (1H, d, J=16.3 Hz, vinyl-H), 7.28 (1H, d, J=1.7 Hz, H-1'), 7.39–7.52 and 7.67–7.71 (13H, 2 sets of m, H-3, H-5, H-3', H-4' and H-biphenyl), 7.98 (2H, d, J=8.4 Hz, H-2 and H-6). Anal. Calcd. for $C_{34}H_{30}O_2$: C 86.78; H 6.43. Found: C 86.85; H 6.45.

4-[(E)-[5,6-Dihydro-5,5-dimethyl-8-4-biphenyl)-2-naphthalenyl]ethenyl]benzoic Acid IR (KBr) $\upsilon_{max}$ (cm$^{-1}$): 3300–2000 (br), 1675 (C=O), 1600. $^1$H NMR 400 MHz (DMSO-d$_6$) δ (ppm): 1.32 (6H, s, 2× —CH$_3$), 2.36 (2H, d, J=4.6 Hz, H-6'), 6.10 (1H, t, J=4.6 Hz, H-7'), 7.11 (1H, d, J=16.4 Hz, vinyl H), 7.17 (1H, d, J=1.6 Hz, H-1'), 7.33 (1H, d, J=16.4 Hz, vinyl H), 7.37–7.52, 7.74–7.77 (10H, 2 sets of m, H-4', H-biphenyl), 7.63 (1H, d, J=8.1 Hz, H-3'), 7.67 (2H, d, J=8.4 Hz, H-3, H-5), 7.86 (2H, d, J=8.4 Hz, H-2, H-6). Anal. Calcd. for $C_{33}H_{28}O_2$ : C 86.81; H 6.18. Found: C 86.74; H 6.16.

EXAMPLE 4

4-[(E)-[5,6-Dihydro-5,5-dimethyl-8-(3-biphenyl)-2-naphthalenyl]ethenyl]benzoic Acid The title material was prepared by the procedure described in Example 1 in using 3-biphenyltrimethyltin. Methyl 4-[(E)-[5,6-dihydro-5,5-dimethyl-8-(3-biphenyl)-2-naphthalenyl]ethenyl]benzoate IR (KBr) $\upsilon_{max}$ (cm$^{-1}$): 3100, 2950, 2910, 1710 (C=O), 1600. $^1$H NMR 400 MHz (CDCl$_3$) δ (ppm): 1.39 (6H, s, 2× —CH$_3$), 2.41 (2H, d, J=4.7 Hz, H-6'), 3.91 (3H, s, —OCH$_3$), 6.10 (1H, t, J=4.7 Hz, H-7'), 6.97 (1H, d, J=16.3 Hz, vinyl-H), 7.12 (1H, d, J=16.3 Hz, vinyl-H), 7.25 (1H, d, J=1.7 Hz, H-1'), 7.36–7.40, 7.42–7.53 and 7.61–7.68 (13H, 3 sets of m, H-3, H-5, H-3', H-4', H-biphenyl) 7.98 (2H, d, J=8.5 Hz, H-2 and H-6). Anal. Calcd. for $C_{34}H_{30}O_2$: C 86.78; H 6.43. Found: C 87.44; H 6.41.

4-[(E)-[5,6-Dihydro-5,5-dimethyl-8-(3-biphenyl)-2-naphthalenyl]ethenyl]benzoic Acid IR (KBr) $\upsilon_{max}$ (cm$^{-1}$): 3700–2000 (br), 1680 (C=O), 1600. $^1$H NMR 400 MHz (DMSO-d$_6$) δ (ppm): 1.33 (6H, s, 2× —CH$_3$), 2.36 (2H, d, J=4.6 Hz, H-6'), 6.14 (1H, t, J=4.6 Hz, H-7'), 7.09 (1H, d, J=16.4 Hz, vinyl H), 7.16 (1H, d, J=0.9 Hz, H-biphenyl), 7.29–7.39, 7.44–7.49, 7.63–7.72 (12H, 3 sets of m, vinyl H, H-3', H-4', H-biphenyl, H-3 and H-5), 7.61 (1H, d, J=1.6 Hz, H-1'), 7.86 (2H, d, J=8.3 Hz, H-2 and H-6). Anal. Calcd. for $C_{33}H_{28}O_2$. 0.55 $H_2O$: C 84.97; H 6.29. Found: C 84.94; H 6.25.

EXAMPLE 5

4-[(E)-(5,6-Dihydro-5,5-dimethyl-8-phenylethynyl-2-naphthalenyl)ethenyl]benzoic Acid The title material was prepared by the procedure described in Example 1 in using 8-phenylethynyltributyltin. Methyl 4-[(E)-(5,6-dihydro-5,5-dimethyl-8-phenylethynyl-2-naphthalenyl)-ethenyl]benzoate IR (KBr) $\upsilon_{max}$ (cm$^{-1}$): 2960, 1715 (C=O), 1600. $^1$H NMR 400 MHz (CDCl$_3$) δ (ppm): 1.33 (6H, s, 2× —CH$_3$), 2.40 (2H, d, J=4.9 Hz, H-6'), 3.94 (3H, s, —OCH$_3$), 6.55 (1H, t, J=4.9 Hz, H-7'), 7.15 (1H, d, J=16.3 Hz, vinyl H), 7.27 (1H, d, J=16.3 Hz, vinyl H), 7.30–7.43 (4H, m, H-3, H-5, H-4' and H-phenyl), 7.48 (1H, dd, J=8.0 and 1.8 Hz, H-3'), 7.58–7.62 (4H, m, H-phenyl), 7.87 (1H, d, J=1.7 Hz, H-1'), 8.03 (2H, d, J=8.3 Hz, H-2 and H-6). Anal. Calcd. for $C_{30}H_{26}O_2$: C 86.09; H 6.26. Found: C 85.88; H 5.90.

4-[(E)-(5,6-Dihydro-5,5-dimethyl-8-phenylethynyl-2-naphthalenyl)ethenyl]benzoic Acid IR (KBr) $\upsilon_{max}$ (cm$^{-1}$): 2960, 1715 (C=O), 1600. $^1$H NMR 400 MHz (DMSO-d$_6$) δ (ppm): 1.27 (6H, s, 2× —CH$_3$), 2.38 (2H, d, J=4.8 Hz, H-6'), 6.60 (1H, t, J=4.8 Hz, H-7'), 7.29 (1H, d, J=16.4 Hz, vinyl H), 7.40–7.48 and 7.63–7.67 (7H, 2 sets of m, H-3', H-4' and H-phenyl), 7.50 (1H, d, J=16.4 Hz, vinyl H), 7.76 (2H, d, J=8.3 Hz, H-3 and H-5), 7.77 (1H, s, H-1'), 7.93 (2H, d, J=8.3 Hz, H-2 and H-6), 12.86 (1H, br s, COOH). Anal. Calcd. for $C_{29}H_{24}O_2$: C 86.11; H 5.98. Found: C 85.81; H 5.73.

EXAMPLE 6

4-[(E)-(5,6-Dihydro-5,5-dimethyl-8-[(Z)-phenylethenyl]-2-naphthalenyl)ethenyl]-benzoic Acid Methyl 4-[(E)-(5,6-dihydro-5,5-dimethyl-8-[(Z)-phenylethenyl]-2-naphthalenyl)-ethenyl]benzoate A stirred solution of methyl 4-[(E)-(5,6-dihydro-5,5-dimethyl-8-phenylethynyl-2-naphthalenyl)ethenyl]benzoate (0.317 g, 0.76 mmol) in pyridine (10 mL) was treated with 10% palladium on barium sulfate and hydrogenated. The mixture was stirred at room temperature for 4 hours, then filtered. The residue was concentrated, diluted with ethyl acetate, washed with 1N hydrochloric acid, saturated sodium bicarbonate and brine. The organic layer was dried over anhydrous magnesium sulfate, filtered and concentrated. The residue was purified by silica gel chromatography (toluene) to give a solid which was triturated in hexane (0.208 g, 65%).

IR (KBr) $\upsilon_{max}$ (cm$^{-1}$): 2965, 1715 (C=O), 1600, 1275. $^1$H NMR 400 MHz (CDCl$_3$) δ (ppm): 1.31 (6H, s, 2× —CH$_3$), 2.22 (2H, dd, J=4.5 and 2.2 Hz, H-6'), 3.93 (3H, s, —OCH$_3$), 5.93 (1H, td, J=4.5 and 1.5 Hz, H-7'), 6.43 (1H, dqa, J=12.0 and 1.9 Hz, vinyl-H-1"), 6.72 (1H, d, J=12.0 Hz, vinyl-H-2"), 7.03 (1H, d, J=16.2 Hz, vinyl H), 7.12–7.22 and 7.35–7.43 (2×4H, 2 sets of m, H-3', H-4', vinyl-H, phenyl), 7.48 (1H, d, J=1.4 Hz, H-1'), 7.55 (2H, d, J=8.3 Hz, H-3 and H-5), 8.02 (2H, d, J=8.4 Hz, H-2 and H-6).

4-[(E)-(5,6-Dihydro-5,5-dimethyl-8-[(Z)-phenylethenyl]-2-naphthalenyl)-ethenyl]benzoic Acid IR (KBr) $\upsilon_{max}$ (cm$^{-1}$): 3600–2700 (br), 1680 (C=O), 1600, 1420, 1290. $^1$H NMR 400 MHz (DMSO-d$_6$) δ (ppm): 1.26 (6H, s, 2× —CH$_3$), 2.19 (2H, dd, J=4.1 and 1.9 Hz, H-6'), 5.87 (1H, br t, J=4.1 Hz, H-7'), 6.49 (1H, dd, J=12.1 and 1.8 Hz, vinyl-H-1"), 6.74 (1H, d, J=12.1 Hz, vinyl-H-2"), 7.12–7.28 and 7.31–7.40 (8H, 2 sets of m, H-3', vinyl H, phenyl), 7.43 (1H, d, J=1.4 Hz, H-1'), 7.53 (1H, d, J=8.0 Hz, H-4'), 7.69 (2H, d, J=8.3 Hz, H-3 and H-5), 7.91 (2H, d, J=8.4 Hz, H-2 and H-6). Anal. Calcd. for C$_{29}$H$_{26}$O$_2$: C 85,68; H 6.45. Found: C 85.04; H 6.19.

EXAMPLE 7

4-[(E)-(5,6-Dihydro-5,5-dimethyl-8-phenylethynyl-2-naphthalenyl)ethynyl]benzoic Acid The title material was prepared by the procedure described in Example 1 by using 8-phenylethynyltributyltin and 4-[(E)-[5,6-dihydro-5,5-dimethyl-8-trifluoromethanesulfonyloxy-2-naphthalenyl]ethynyl]benzoate.

Ethyl 4-[(E)-(5,6-dihydro-5,5-dimethyl-8-phenylethynyl-2-naphthalenyl)-ethynyl]benzoate IR (KBr) $\upsilon_{max}$ (cm$^{-1}$): 2990, 1715 (C=O), 1605, 1275. $^1$H NMR 400 MHz (CDCl$_3$) δ (ppm): 1.33 (6H, s, 2× —CH$_3$), 1.42 (3H, t, J=7.1 Hz, —OCH$_2$CH$_3$), 2.40 (2H, d, J=4.8 Hz, H-6'), 4.40 (2H, qa, J=7.1 Hz, —OCH$_2$—), 7.33 (1H, d, J=8.0 Hz, H-4'), 7.32–7.40 (4H, m, phenyl), 7.46 (1H, dd, J=8.0 and 1.6 Hz, H-3'), 7.59 (1H, dd, J=7.7 and 1.5 Hz, phenyl), 7.61 (1H, d, J=8.4 Hz, H-3 and H-5), 7.87 (1H, d, J=1.5 Hz, H-1'), 8.03 (2H, d, J=8.3 Hz, H-2 and H-6).

4-[(E)-(5,6-Dihydro-5,5-dimethyl-8-phenylethynyl-2-naphthalenyl)ethynyl]benzoic Acid IR (KBr) $\upsilon_{max}$ (cm$^{-1}$): 3650–2250 (br), 1680, 1605. $^1$H NMR 400 MHz (DMSO-d$_6$) δ (ppm): 1.27 (6H, s, 2× —CH$_3$), 2.41 (2H, d, J=4.8 Hz, H-6'), 6.64 (1H, t, J=4.8 Hz, H-7'), 7.44–7.47 and 7.60–7.62 (4H and 2H, 2 sets of m, phenyl and H-4'), 7.55 (1H, dd, J=8.0 and 1.7 Hz, H-3'), 7.69 (2H, d, J=8.3 Hz, H-3 and H-5), 7.72 (1H, d, J=1.7 Hz, H-1'), 7.96 (2H, d, J=8.4 Hz, H-2 and H-6).

Anal. Calcd. for C$_{29}$H$_{22}$O$_2$.0.25 H$_2$O: C 85,58; H 5.47. Found: C 85.55; H 5.80.

EXAMPLE 8

4-[(E)-(5,6-Dihydro-5,5-dimethyl-8-4-methylphenylethynyl)-2-naphthalenyl)-ethenyl]benzoic Acid The title material was prepared by the procedure described in Example 1 by using 4-methylphenylethynyltributyltin.

Methyl 4-[(E)-(5,6-dihydro-5,5-dimethyl-8-4-methylphenylethynyl)-2-naphthalenyl)ethenyl]benzoate IR (KBr) $\upsilon_{max}$ (cm$^{-1}$): 2950, 1715 (C=O), 1605. $^1$H NMR 400 MHz (CDCl$_3$) δ (ppm): 1.33 (6H, s, 2× —CH$_3$), 2.40 (2H, d overlapped by —CH$_3$, H-6'), 2.41 (3H, s, —CH$_3$), 3.94 (3H, s, —OCH$_3$), 6.52 (1H, t, J=4.8 Hz, H-7'), 7.14 (1H, d, J=16.3 Hz, vinyl H), 7.26 (1H, d, J=16.3 Hz, vinyl H), 7.12–7.28 and 7.45–7.50 (5H, 2 sets of m, H-3' and H-tolyl), 7.34 (1H, d, J=8.0 Hz, H-4'), 7.58 (2H, d, J=8.4 Hz, H-3 and H-5), 7.87 (1H, d, J=1.6 Hz, H-1'), 8.03 (2H, d, J=8.3 Hz, H-2 and H-6). Anal. Calcd. for C$_{31}$H$_{28}$O$_2$. 0.4 H$_2$O: C 84.67; H 6.60. Found: C 84.69; H 6.34.

4-[(E)-(5,6-Dihydro-5,5-dimethyl-8-4-methylphenylethynyl)-2-naphthalenyl)ethenyl]benzoic Acid IR (KBr) $\upsilon_{max}$ (cm$^{-1}$): 3650–2300 (br), 2960, 1670 (C=O), 1605. $^1$H NMR 400 MHz (DMSO-d$_6$) δ (ppm): 1.26 (6H, s, 2× —CH$_3$), 2.36 (3H, s, —CH$_3$), 2.37 (2H, d overlapped by —CH$_3$, H-6'), 6.56 (1H, t, J=4.8 Hz, H-7'), 7.26–7.30 and 7.48–7.55 (6H, 2 sets of m, vinyl H, H-tolyl), 7.41 (1H, d, J=8.1 Hz, H-4'), 7.66 (1H, d, J=8.1 Hz, H-3'), 7.75 (2H, d, J=8.3 Hz, H-3 and H-5), 7.76 (1H, s, H-1'), 7.93 (2H, d, J=8.3 Hz, H-2 and H-6). Anal. Calcd. for C$_{30}$H$_{26}$O$_2$.0.5 H$_2$O: C 84.28; H 6.37. Found: C 84.38; H 6.34.

EXAMPLE 9

4-[(E)-(5,6-Dihydro-5,5-dimethyl-8-4-fluorophenylethynyl)-2-naphthalenyl)-ethenyl]benzoic Acid The title material was prepared by the procedure described in Example 1 by using 4-fluorophenylethynyltributyltin.

Methyl 4-[(E)-(5,6-dihydro-5,5-dimethyl-8-4-fluorophenylethynyl)-2-naphthalenyl)ethenyl]benzoate IR (KBr) $\upsilon_{max}$ (cm$^{-1}$): 2950, 1710 (C=O), 1605. $^1$H NMR 400 MHz (CDCl$_3$) δ (ppm): 1.33 (6H, s, 2× —CH$_3$), 2.40 (2H, d, J=4.8 Hz, H-6'), 3.94 (3H, s, —OCH$_3$), 6.54 (1H, t, J=4.8 Hz, H-7'), 7.07–7.15 (2H, m, H-phenyl), 7.14 (1H, d, J=16.1 Hz, vinyl H), 7.23–7.27 (1H, d overlapped by CDCl$_3$, vinyl H), 7.35 (1H, d, J=8.0 Hz, H-4'), 7.48 (1H, dd, J=8.0 and 1.5 Hz, H-3'), 7.55–7.59 (2H, m, H-phenyl), 7.58 (2H, d, J=8.3 Hz, H-3 and H-5), 7.82 (1H, d, J=1.5 Hz, H-1'), 8.03 (2H, d, J=8.4 Hz, H-2 and H-6). Anal. Calcd. for C$_{30}$H$_{25}$O$_2$F: C 82.54; H 5.77; F 4.35. Found: C 82.20; H 5.84; F 4.15.

4-[(E)-(5,6-Dihydro-5,5-dimethyl-8-4-fluorophenylethynyl)-2-naphthalenyl)ethenyl]benzoic Acid IR (KBr) $\upsilon_{max}$ (cm$^{-1}$): 3650–2300 (br), 2950, 1660 (C=O), 1600. $^1$H NMR 400 MHz (DMSO-d$_6$) δ (ppm): 1.26 (6H, s, 2× —CH$_3$), 2.38 (2H, d, J=4.7 Hz, H-6'), 6.59 (1H, t, J=4.7 Hz, H-7'), 7.28 (1H, d, J=16.3 Hz, vinyl H), 7.27–7.33 (2H, m, H-phenyl), 7.41 (1H, d, J=8.0 Hz, H-4'), 7.50 (1H, d, J=16.3 Hz, vinyl H), 7.66 (1H, d, J=8.0 Hz, H-3'), 7.70–7.76 (3H, m, H-1' and H-phenyl), 7.75 (2H, d, J=8.2 Hz, H-3 and H-5), 7.93 (2H, d, J=8.2 Hz, H-2 and H-6). Anal. Calcd. for $C_{29}H_{23}O_2F$. 0.1 $H_2O$: C 82.09; H 5.51. Found: C 82.1; H 5.6.

EXAMPLE 10

4-[(E)-(5,6-Dihydro-5,5-dimethyl-8-(3-pyridinyl-ethynyl)-2-naphthalenyl)-ethenyl]benzoic Acid The title material was prepared by the procedure described in Example 1 using tributyl(3-pyridinylethynyl) tin.

Methyl 4-[(E)-(5,6-dihydro-5,5-dimethyl-8-(3-pyridinyl-ethynyl-2-naphthalenyl)ethenyl]benzoate IR (KBr) $\upsilon_{max}$ (cm$^{-1}$): 3100–2800 (w, aromatic, aliphatic), 1715 (s, C=O), 1600 (s, C=C). $^1$H NMR 400 MHz (CDCl$_3$) δ (ppm): 8.83 (d, J=1.7 Hz, 1H, H-2 in pyridyl), 8.58 (dd, J=4.8, 1.4 Hz, 1H, H-6 in pyridyl), 8.02 (d, J=8.3 Hz, 2H, H-2, H-6), 7.85 (ddd, J=7.8, 1.9, 1.9 Hz, 1H, H-4 in pyridyl), 7.80 (d, J=1.5 Hz, 1H, H-1'), 7.57 (d, J=8.3 Hz, 2H, H-3, H-5), 7.48 (dd, J=8.0, 1.6 Hz, 1H, H-3'), 7.35 (d, J=8.2 Hz, 1H, H-4'), 7.32 (dd, J=7.9, 3.0 Hz, 1H, H-5 in pyridyl), 7.24 (d, J=16.3 Hz, 1H, vinyl H), 7.12 (d, J=16.3 Hz, 1H, vinyl H), 6.59 (t, J=4.8 Hz, 1H, H-7'), 3.92 (s, 3H, CO$_2$CH$_3$), 2.40 (d, J=4.8 Hz, 2H, H-6'), 1.56 (s, 6H, 2× CH$_3$).

4-[(E)-(5,6-Dihydro-5,5-dimethyl-8-(3-pyridinyl-ethynyl)-2-naphthalenyl)ethenyl]benzoic Acid IR (KBr) $\upsilon_{max}$ (cm$^{-1}$): 3600–2100 (br, s, CO$_2$H, aromatic, aliphatic), 2220 (w, acetylene), 1690 (s, C=O), 1605 (s, C=C). $^1$H NMR 400 MHz (DMSO-d$_6$) δ (ppm): 8.86 (s, 1H, H-2 in pyridyl), 8.60 (dd, J=4.9, 1.5 Hz, 1H, H-6 in pyridyl), 8.06 (d, J=8.0 Hz, 1H, H-4 in pyridyl), 7.92 (d, J=8.3 Hz, 2H, H-2, H-6), 7.77 (d, J=1.5 Hz, 1H, H-1'), 7.75 (d, J=8.3 Hz, 2H, H-3, H-5), 7.67 (d, J=8.1 Hz, 1H, H-3'), 7.51 (d, J=16.8 Hz, 1H, vinyl H), 7.49 (dd, J=7.3, 7.3 Hz, 1H, H-5 in pyridyl), 7.41 (d, J=8.1 Hz, 1H, H-4'), 7.30 (d, J=16.5 Hz, 1H, vinyl H), 6.65 (t, J=4.8 Hz, 1H, H-7'), 2.39 (d, J=4.9 Hz, 2H, H-6'), 1.26 (s, 6H, 2× CH$_3$). Anal. Calcd for $C_{28}H_{23}NO_2$.0.5 $H_2O$: C,81.13; H, 5.84; N, 3.38. Found: C, 81.21; H, 5.93; N, 3.32.

EXAMPLE 11

4-[(E)-(5,6-Dihydro-5,5-dimethyl-8-4-(imidazol-1-yl)phenyl)-2-naphthalenyl)ethenyl]benzoic Acid The title material was prepared as described in Example 1 using tributyl-4-(imidazol-1-yl)phenyl)tin.

Methyl 4-[(E)-(5,6-dihydro-5,5-dimethyl-8-4-(imidazol-1-yl)phenyl)-2-naphthalenyl)ethenyl]benzoate IR (KBr) $\upsilon_{max}$ (cm$^{-1}$): 3100–2800(w, aromatic, aliphatic), 1700 (s, C=O), 1600 (s, C=C). $^1$H NMR 400 MHz (CDCl$_3$) δ (ppm): 7.97 (d, J=8.3 Hz, 2H, H-2, H-6), 7.94 (s, 1H, H-2 in imidazole), 7.51–7.40 (m, 8H, H-5, H-3, H-4'-H-3', phenyl in 8'), 7.36 (s, 1H, H-4 or H-5 in imidazole), 7.25 (s, 1H, H-4 or H-5 in imidazole), 7.13 (d, J=1.5 Hz, 1H, H-1'), 7.10 (d, J=16.4 Hz, 1H, vinyl H), 6.95 (d, J=16.3 Hz, 1H, vinyl H), 6.07 (t, J=4.6 Hz, 1H, H-7'), 3.90 (s, 3H, CO$_2$CH$_3$), 2.39 (d, J=4.7 Hz, 2H, H-6'), 1.37 (s, 6H, 2× CH$_3$).

4-[(E)-(5,6-Dihydro-5,5-dimethyl-8-4-(imidazol-1-yl)phenyl)-2-naphthalenyl)ethenyl]benzoic Acid IR (KBr) $\upsilon_{max}$ (cm$^{-1}$): 3700–2200 (br, S, CO$_2$H, HCl, aromatic, aliphatic), 1680 (s, C=O), 1605 (s, C=C). $^1$H NMR 400 MHz (DMSO-d$_6$) δ (ppm): 8.26 (s, 1H, H-2 in imidazole), 7.86 (d, J=8.2 Hz, 2H, H-2, H-6), 7.85 (two sets of doublets, 4H), 7.79 (s, 1H, H-5 or H-4 in imidazole), 7.61 (two sets of doublets, 4H), 7.61 (s, 1H, H-5 or H-4 in imidazole), 7.29 (d, J=16.5 Hz, 1H, vinyl H), 7.09 (d, J=16.4 Hz, 1H, vinyl H), 7.09 (s, 1H, H-1'), 6.13 (t, J=4.5 Hz, 1H, H-7'), 2.36 (d, J=4.5 Hz, 2H, H-6'), 1.31 (s, 6H, 2× CH$_3$). Anal. Calcd for $C_{30}H_{26}N_2O_2$.2.8 $H_2O$.HCl: C,67.55; H, 6.16; N, 5.25. Found: C, 67.53; H, 6.08; N, 4.91.

EXAMPLE 12

4-[(E)-(5,6-Dihydro-5,5-dimethyl-8-(4-(2-formyl) thiophenyl)-2-naphthalenyl)ethenyl]benzoic Acid The title material was prepared as described in Example 1 using tributyl(4-(2-formyl)thioophenyl)tin.

Methyl 4-[(E)-(5,6-dihydro-5,5-dimethyl-8-4-(2-formyl) thiophenyl)-2-naphthalenyl)ethenyl]benzoate IR (KBr) $\upsilon_{max}$ (cm$^{-1}$): 3100–2800 (w, aromatic, aliphatic), 1715 (s, C=O), 1680 (s, C=O), 1600 (s, C=C). $^1$H NMR 400 MHz (CDCl$_3$) δ (ppm): 9.96 (s, 1H, CHO), 7.99 (d, J=8.3 Hz, 2H, H-2, H-6), 7.81 (s, 1H, H-3 in thiophene), 7.70 (s, 1H, H-5 in thiophene), 7.51 (d, J=8.3 Hz, 2H, H-3, H-5), 7.47 (dd, J=7.9, 1.2 Hz, 1H, H-3'), 7.40 (d, J=8.0 Hz, 1H, H-4'), 7.19 (d, J=1.2 Hz, 1H, H-1'), 7.12 (d, J=16.4 Hz, 1H, vinyl H), 6.98 (d, J=16.3 Hz, 1H, vinyl H), 6.14 (t, J=4.7 Hz, 1H, H-7'), 3.91 (s, 3H, CO$_2$CH$_3$), 2.36 (d, J=4.7 Hz, 2H, H-6'), 1.34 (s, 6H, 2× CH$_3$).

4-[(E)-(5,6-Dihydro-5,5-dimethyl-8-4-(2-formyl) thiophenyl)-2-naphthalenyl)ethenyl]benzoic Acid IR (KBr) $\upsilon_{max}$ (cm$^{-1}$): 3700–2200(br, s, CO$_2$H, aromatic, aliphatic), 1680 (s, C=O, aldehyde and ester), 1600 (s, C=C). $^1$H NMR 400 MHz (DMSO-d$_6$) δ (ppm): 9.98 (s, 1H, CHO), 8.11 (d, J=8.5 Hz, 2H, H-2, H-6), 7.90 (s, 1H, H-3 or H-5 in thiophene); 7.88 (s, 1H, H-3 or H-5 in thiophene), 7.68 (d, J=8.2 Hz, 2H, H-3, H-5), 7.64 (d, J=8.0 Hz, 1H, H-4' or H-3'), 7.44 (d, J=8.0 Hz, 1H, H-4' or H-3'), 7.37 (d, J=16.5 Hz, 1H, vinyl H), 7.25 (s, 1H, H-1'), 7.16 (d, J=16.5 Hz, 1H, vinyl H), 6.23 (t, J=4.8 Hz, 1H, H-7'), 2.33 (d, J=4.7 Hz, 2H, H-6'), 1.29 (s, 6H, 2× CH$_3$). Anal. Calcd for $C_{26}H_{22}O_3S$.0.6 $H_2O$: C,73.42; H, 5,50. Found: C, 73.76; H, 5,67.

EXAMPLE 13

4-[(E)-(5,6-Dihydro-5,5-dimethyl-8-(5-(2-methoxy-pyridinyl)-2-naphthalenyl)ethenyl]benzoic Acid The title material was prepared as described in Example 1 using tributyl(5-(2-methoxy-pyridyl)tin.

Methyl 4-[(E)-(5,6-dihydro-5,5-dimethyl-8-(5-(2-methoxy-pyridinyl)-2-naphthalenyl)ethenyl]benzoate $^1$H NMR 400 MHz (CDCl$_3$) δ (ppm): 8.19 (s, 1H, H-6 in pyridyl), 7.99 (d, J=8.3 Hz, 2H, H-2, H-6), 7.59–7.38 (m, 3H, H-3 and H-4 in pyridyl and H-3), 7.51 (d, J=8.3 Hz, 2H, H-3, H-5), 7.10 (d, J=16.2 Hz, 1H, vinyl H), 7.10 (s, 1H, H-1'), 6.95 (d, J=16.3 Hz, 1H, vinyl H), 6.81 (d, J=8.4 Hz, 1H, H-4'), 6.01 (t, J=4.6 Hz, 1H, H-7'), 4.01 (s, 3H, OCH$_3$), 3.92 (s, 3H, CO$_2$CH$_3$), 2.38 (d, J=4.6 Hz, 2H, H-6'), 1.36 (s, 6H, 2× CH$_3$).

4-[(E)-(5,6-Dihydro-5,5-dimethyl-8-(5-(2-methoxy-pyridinyl)-2-naphthalenyl)ethenyl]benzoic Acid IR (KBr) $\upsilon_{max}$ (cm$^{-1}$): 3600–2300(br, s, CO$_2$H, aromatic, aliphatic), 1675 (s, C=O), 1600 (s, C=C). $^1$H NMR 400 MHz (DMSO-d$_6$) δ (ppm): 8.14 (s, 1H, H-5 in pyridyl), 7.87 (d, J=7.2 Hz, 2H, H-2, H-6), 7.69 (d, J=9.8 Hz, 2H, H-3, H-5), 7.66 (m, 1H), 7.61 (d, J=8.1 Hz, 1H), 7.43 (d, J=7.7

Hz, 1H), 7.32 (d, J=16.4 Hz, 1H, vinyl H), 7.11 (d, J=16.4 Hz, 1H, vinyl H), 7.04 (s, 1H, H-1'), 6.88 (d, J=7.7 Hz, 1H), 6.04 (t, J=4.5 Hz, 1H, H-7'), 3.90 (s, 3H, $OCH_3$), 2.32 (d, J=4.1 Hz, 2H, H-6'), 1.30 (s, 6H, 2× $CH_3$). Anal. Calcd for $C_{27}H_{25}NO_3$.0.8 $H_2O$: C,76.14; H, 6.30; N, 3.29. Found: C, 75.90; H, 6.11; N, 3.05.

EXAMPLE 14

4-[(E)-(5,6-Dihydro-5,5-dimethyl-8-(indol-5-yl)-2-naphthalenyl)ethenyl]benzoic Acid The title material was prepared as described in Example 1 using tributyl(indol-5-yl) tin.

Methyl 4-[(E)-(5,6-dihydro-5,5-dimethyl-8-(indol-5-yl)-2-naphthalenyl)ethenyl]benzoate IR (KBr) υmax($cm^{-1}$): 3400 (s, amine), 3100–2800(w, aromatic, aliphatic), 1710 (s, C=O), 1600 (s, C=C). $^1H$ NMR 400 MHz ($CDCl_3$) δ (ppm): 8.22 (br s, 1H), 7.94 (d, J=8.2 Hz, 2H, H-2, H-6), 7.66 (s, 1H), 7.46–7.37 (m, 3H), 7.43 (d, J=8.0 Hz, 2H, H-3, H-5), 7.26–7.20 (m, 2H), 7.07 (d, J=16.3 Hz, 1H, vinyl H), 6.91 (d, J=16.3 Hz, 1H, vinyl H), 6.59 (br s, 1H), 6.03 (t, J=4.5 Hz, 1H, H-7'), 3.85 (s, 3H, $CO_2CH_3$), 2.38 (d, J=4.6 Hz, 2H, H-6'), 1.38 (s, 6H, 2× $CH_3$).

4-[(E)-(5,6-Dihydro-5,5-dimethyl-8-(indol-5-yl)-2-naphthalenyl)ethenyl]benzoic Acid IR (KBr) $υ_{max}$ ($cm^{-1}$): 3380 (m, amine), 3500–2200(br, m, $CO_2H$, aromatic, aliphatic), 1685 (s, C=O), 1605 (s, C=C). $^1H$ NMR 400 MHz (DMSO-$d_6$) δ (ppm): 7.82 (d, J=8.4 Hz, 2H, H-2, H-6), 7.62 (d, J=8.4 Hz, 2H, H-3, H-5), 7.58 (dd, J=8.1, 1.6 Hz, 1H), 7.50 (s, 1H), 7.43 (d, J=5,5 Hz, 1H), 7.41 (d, J=5.2 Hz, 1H), 7.36 (dd, J=2.8, 2.8 Hz, 1H), 7.24 (d, J=16.4 Hz, 1H, vinyl H), 7.13 (d, J=1.6 Hz, 1H), 7.03 (d, J=16.7 Hz, 1H, vinyl H), 7.02 (dd, J=8.9, 1.5 Hz, 1H), 6.44 (br s, 1H), 5.96 (t, J=4.6 Hz, 1H, H-7'), 2.32 (d, J=4.6 Hz, 2H, H-6'), 1.32 (s, 6H, 2× $CH_3$). Anal. Calcd for $C_{29}H_{25}NO_2$.0.7 $H_2O$: C,80.60; H, 6.16; N, 3.24. Found: C, 80.63; H, 6.37; N, 3.06.

EXAMPLE 15

4-[(E)-(5,6-Dihydro-5,5-dimethyl-8-(5-(2-dimethylamino)pyridinyl)-2-naphthalenyl)ethenyl]benzoic Acid The title material was prepared as described in Example 1 using tributyl(5-(2-dimethylamino)pyridinyl)tin.

Methyl 4-[(E)-(5,6-dihydro-5,5-dimethyl-8-(5-(2-dimethylamino)pyridinyl)-2-naphthalenyl)ethenyl]benzoic Acid IR (KBr) $υ_{max}$ ($cm^{-1}$): 3100–2800 (w, aromatic, aliphatic), 1710 (s, C=O), 1600 (s, C=C), 1270 (s, tertiary amine). $^1H$ NMR 400 MHz ($CDCl_3$) δ (ppm): 8.21 (d, J=2.3 Hz, 1H, H-6 in pyridyl), 7.98 (d, J=8.3 Hz, 2H, H-2, H-6), 7.50 (d, J=8.4 Hz, 2H, H-3, H-5), 7.46 (dd, J=8.7, 2.4 Hz, 1H, H-4 in pyridyl), 7.43 (dd, J=8.1, 1.7 Hz, 1H, H-3'), 7.37 (d, J=8.0 Hz, 1H, H-4'), 7.19 (d, J=1.5 Hz, 1H, H-1'), 7.11 (d, J=16.3 Hz, 1H, vinyl H), 6.96 (d, J=16.3 Hz, 1H, vinyl H), 6.58 (d, J=8.7 Hz, 1H, H-3 in pyridyl), 5.96 (t, J=4.6 Hz, 1H, H-7'), 3.91 (s, 3H, $CO_2CH_3$), 3.15 (s, 6H, N($CH_3)_2$), 2.34 (d, J=4.7 Hz, 2H, H-6'), 1.34 (s, 6H, 2× $CH_3$).

4-[(E)-(5,6-Dihydro-5,5-dimethyl-8-(5-(2-dimethylamino)pyridinyl)-2-naphthalenyl)ethenyl]benzoic Acid IR (KBr) $υ_{max}$ ($cm^{-1}$): 3700–2100 (br, s, $CO_2H$, HCl, aromatic, aliphatic), 1680, 1655 (s, C=O), 1605 (s, C=C), 1290 (tertiary amine). $^1H$ NMR 400 MHz (DMSO-$d_6$) δ (ppm): 7.93 (d, J=8.0 Hz, 1H, H-4 in pyridyl, 7.91 (d, J=2.0 Hz, 1H, H-6 in pyridyl), 7.89 (d, J=8.7 Hz, 2H, H-2, H-6), 7.65 (d, J=7.7 Hz, 2H, H-3, H-5), 7.61 (d, J=8.1 Hz, 1H, H-3'), 7.44 (d, J=8.0 Hz, 1H, H-4'), 7.31 (d, J=16.5 Hz, 1H, vinyl H), 7.28 (d, J=9.5 Hz, 1H, H-3 in pyridyl), 7.17 (d, J=16.4 Hz, 1H, vinyl H), 7.09 (s, 1H, H-1'), 6.14 (t, J=4.2 Hz, 1H, H-7'), 3.27 (s, 6H, N($CH_3)_2$), 2.34 (d, J=4.3 Hz, 2H, H-6'), 1.30 (s, 6H, 2× $CH_3$). Anal. Calcd for $C_{28}H_{28}N_2O_2$.2.0 $H_2O$.HCl: C,67.66; H, 6.69; N, 5,64. Found: C, 67.62; H, 6.66; N, 5.47.

EXAMPLE 16

4-[(E)-(5,6-Dihydro-5,5-dimethyl-8-(5-(2-aminopyridinyl))-2-naphthalenyl)ethenyl]benzoic Acid Methyl 4-[(E)-(5,6-dihydro-5,5-dimethyl-8-(5-(2-aminopyridinyl))-2-naphthalenyl)ethenyl]benzoate IR (KBr) $υ_{max}$ ($cm^{-1}$): 3480 (w, amine), 3100–2800(w, aromatic, aliphatic), 1715 (s, C=O), 1600 (s, C=C), 1280 (s, amine). $^1H$ NMR 400 MHz ($CDCl_3$) δ (ppm): 8.11 (d, J=1.9 Hz, 1H, H-6 in pyridyl), 7.98 (d, J=8.4 Hz, 2H, H-2, H-6), 7.51 (d, J=8.5 Hz, 2H, H-3, H-5), 7.45 (dd, J=8.3, 2.2 Hz, 1H, H-3 in pyridyl), 7.43 (dd, J=7.2, 1.7 Hz, 1H, H-3'), 7.37 (d, J=8.0 Hz, 1H, H-4'), 7.16 (d, J=1.6 Hz, 1H, H-1'), 7.11 (d, J=16.4 Hz, 1H, vinyl H), 6.96 (d, J=16.3 Hz, 1H, vinyl H), 6.57 (d, J=8.8 Hz, 1H, H-4 in pyridyl), 5.98 (t, J=4.7 Hz, 1H, H-7'), 3.91 (s, 3H, $CO_2CH_3$), 2.35 (d, J=4.7 Hz, 2H, H-6'), 1.29 (s, 6H, 2× $CH_3$).

4-[(E)-(5,6-Dihydro-5,5-dimethyl-8-(5-(2-aminopyridinyl))-2-naphthalenyl)ethenyl]benzoic Acid IR (KBr) $υ_{max}$ ($cm^{-1}$): 3700–2000 (br, s, $CO_2H$, HCl, aromatic, aliphatic, amine), 1670 (s, C=O), 1600 (s, C=C), 1280 (amine). $^1H$ NMR 400 MHz (DMSO-$d_6$) δ (ppm): 7.95 (s, 1H, H-6 in pyridyl), 7.91 (d, J=7.6 Hz, 2H, H-2, H-6), 7.87 (d, J=9.0 Hz, 1H, H-4 in pyridyl), 7.66 (d, J=7.9 Hz, 2H, H-3, H-5), 7.61 (d, J=8.1 Hz, 1H, H-3'), 7.43 (d, J=8.1 Hz, 1H, H-4'), 7.34 (d, J=16.5 Hz, 1H, vinyl H), 7.19 (d, J=16.4 Hz, 1H, vinyl H), 7.12 (s, 1H, H-1'), 7.02 (d, J=9.1 Hz, 1H, H-3 in pyridyl), 6.12 (t, J=4.4 Hz, 1H, H-7'), 2.32 (d, J=4.3 Hz, 2H, H-6'), 1.29 (s, 6H, 2× $CH_3$). Anal. Calcd for $C_{26}H_{24}N_2O_2$.0.5 $H_2O$.HCl: C,70.66; H, 5.93; N, 6.34. Found: C, 70.63; H, 5.92; N, 5.97.

EXAMPLE 17

4-[(E)-(5,6-Dihydro-5,5-dimethyl-8-(2-benzofuryl)-2-naphthalenyl)ethenyl]benzoic Acid The title material was prepared as described in Example 1 using tributyl(2-benzofuryl)tin.

Methyl 4-[(E)-(5,6-dihydro-5,5-dimethyl-8-(2-benzofuryl)-2-naphthalenyl)-ethenyl]benzoic Acid IR (KBr) $υ_{max}$ ($cm^{-1}$): 3100–2800(w, aromatic, aliphatic), 1715 (s, C=O), 1605 (s, C=C). $^1H$ NMR 400 MHz ($CDCl_3$) δ (ppm): 8.00 (d, J=8.4 Hz, 2H, H-2, H-6), 7.69 (d, J=1.6 Hz, 1H), 7.62 (dd, J=7.3, 1.0 Hz, 1H), 7.54 (d, J-8.3 Hz, 2H, H-3, H-5), 7.53 (d, J=7.6 Hz, 1H), 7.49 (dd, J=8.0, 1.7 Hz, 1H), 7.41 (d, J=8.0 Hz, 1H), 7.31 (ddd, J=7.2, 7.2, 1.3 Hz, 1H, H-5 or H-6 in benzofuryl), 7.26 (ddd, J=7.2, 7.2, 1.0 Hz, 1H, H-5 or H-6 in benzofuryl), 7.20 (d, J=16.3 Hz, 1H, vinyl H), 7.05 (d, J=16.3 Hz, 1H, vinyl H), 6.86 (s, 1H), 6.67 (t, J=5.0 Hz, 1H, H-7'), 3.91 (s, 3H, $CO_2CH_3$), 2.41 (d, J=5.0 Hz, 2H, H-6'), 1.35 (s, 6H, 2× $CH_3$).

4-[(E)-(5,6-Dihydro-5,5-dimethyl-8-(2-benzofuryl)-2-naphthalenyl)ethenyl]benzoic Acid IR (KBr) $υ_{max}$ ($cm^{-1}$): 3700–2100 (br, S, $CO_2H$, aromatic, aliphatic), 1680 (s, C=O), 1600 (s, C=C). $^1H$ NMR 400 MHz (DMSO-d$_6$) δ (ppm): 7.88 (d, J=7.8 Hz, 2H, H-2, H-6), 7.69 (d, J=7.9 Hz, 2H, H-3, H-5), 7.67–7.65 (m, 3H), 7.60 (d, J=7.9 Hz, 1H), 7.46 (d, J=7.6 Hz, 1H), 7.43 (d, J=15.9 Hz, 1H, vinyl H), 7.33 (dd, J=7.3, 7.3 Hz, 1H, H-5 or H-6 in benzofuryl), 7.27 (dd, J=7.4, 7.4 Hz, 1H, H-5 or H-6 in benzofuryl), 7.23 (d, J=16.7 Hz, 1H, vinyl H), 7.10 (s, 1H), 6.69 (t, J=4.7 Hz, 1H, H-7'), 2.39 (d, J=4.8 Hz, 2H, H-6'), 1.29 (s, 6H, 2× CH$_3$). Anal. Calcd for C$_{29}$H$_{24}$O$_3$.0.5 H$_2$O: C,81.10; H, 5.87. Found: C, 80.86; H, 5.80.

EXAMPLE 18

4-[(E)-(5,6-Dihydro-5,5-dimethyl-8-(1-naphthalenyl)-2-naphthalenyl)ethenyl]benzoic Acid Methyl 4-[(E)-(5,6-dihydro-5,5-dimethyl-8-(1-naphthalenyl)-2-naphthalenyl)ethenyl]benzoic Acid IR (KBr) υ$_{max}$ (cm$^{-1}$): 3100–2800(w, aromatic, aliphatic), 1715 (s, C=O), 1605 (s, C=C). $^1$H NMR 400 MHz (CDCl$_3$) δ (ppm): 7.92–7.88 (m, 2H), 7.90 (d, J=8.4 Hz, 2H, H-2, H-6), 7.76 (d, J=8.4 Hz, 1H), 7.54 (dd, J=7.1, 7.1 Hz, 1H), 7.48–7.41 (m, 4H), 7.36 (d, J=8.3 Hz, 2H, H-3, H-5), 7.33 (m, 1H), 6.89 (d, J=16.3 Hz, 1H, vinyl H), 6.75 (d, J=16.3 Hz, 1H, vinyl H), 6.67 (s, 1H), 6.07 (t, J=4.6 Hz, 1H, H-7'), 3.88 (s, 3H, CO$_2$CH$_3$), 2.52 (dd, J=17.0, 4.1 Hz, 1H, H-6'), 2.46 (dd, J=17.1, 5.0 Hz, 1H, H-6'), 1.48 (s, 6H, 2× CH$_3$).

4-[(E)-(5,6-Dihydro-5,5-dimethyl-8-(1-naphthalenyl)-2-naphthalenyl)-ethenyl]benzoic Acid IR (KBr) υ$_{max}$ (cm$^{-1}$): 3300–2300 (br, s, CO$_2$H, aromatic, aliphatic), 1675 (s, C=O), 1600 (s, C=C). $^1$H NMR 400 MHz (DMSO-d$_6$) δ (ppm): 8.00 (d, J=8.1 Hz, 1H), 7.99 (d, J=8.2 Hz, 1H), 7.79 (d, J=8.3 Hz, 2H, H-2, H-6), 7.64–7.39 (m, 9H, naphthalenyl and H-5, H-3, H-3', H-4'), 7.04 (d, J=16.2 Hz, 1H, vinyl H), 6.91 (d, J=16.4 Hz, 1H, vinyl H), 6.53 (s, 1H, H1'), 6.06 (t, J=4.6 Hz, 1H, H-7'), 2.46 (d, J=6.2 Hz, 2H, H-6'), 1.45 (s, 3H, CH$_3$), 1.43 (s, 3H, CH$_3$). Anal. Calcd for C$_{31}$H$_{26}$O$_2$.0.5 H$_2$O: C,84.71; H, 6.19. Found: C, 84.93; H, 6.28.

EXAMPLE 19

4-[(E)-(5,6-Dihydro-5,5-dimethyl-8-(4-isoquinolyl)-2-naphthalenyl)ethenyl]benzoic Acid The title material was prepared as described in Example 1 using tributyl(4-isoquinolyl)tin.

Methyl 4-[(E)-(5,6-dihydro-5,5-dimethyl-8-4-isoquinolyl)-2-naphthalenyl)-ethenyl]benzoic Acid IR (KBr) υ$_{max}$ (cm): 3100–2800 (w, aromatic, aliphatic), 1720 (s, C=O), 1605 (s, C=C). $^1$H NMR 400 MHz (CDCl$_3$) δ (ppm): 9.32 (br s, 1H), 8.50 (br s, 1H), 8.07 (dd, J=6.9, 2.0 Hz, 1H), 7.91 (d, J=8.4 Hz, 2H, H-2, H-6), 7.69 (dd, J=7.2, 1.8 Hz, 1H), 7.64–7.59 (m, 2H), 7.44 (s, 2H), 7.37 (d, J=8.3 Hz, 2H, H-3, H-5), 6.89 (d, J=16.3 Hz, 1H, vinyl H), 6.75 (d, J=16.3 Hz, 1H, vinyl H), 6.65 (s, 1H), 6.15 (t, J=5.1 Hz, 1H, H-7'), 3.88 (s, 3H, CO$_2$CH$_3$), 2.57 (dd, J=17.1, 3.7 Hz, 1H, H-6'), 2.46 (dd, J=17.1, 5.4 Hz, 1H, H-6'), 1.50 (s, 3H, CH$_3$), 1.46 (s, 3H, CH$_3$).

4-[(E)-(5,6-Dihydro-5,5-dimethyl-8-4-isoquinolyl)-2-naphthalenyl)ethenyl]benzoic Acid IR (KBr) υ$_{max}$ (cm$^{-1}$): 3700–2200 (br, s, CO$_2$H, HCl, aromatic, aliphatic), 1710 (s, C=O), 1600 (s, C=C). $^1$H NMR 400 MHz (DMSO-d$_6$) δ (ppm): 9.60 (s, 1H), 8.52 (s, 1H), 8.36 (d, J=7.8 Hz, 1H), 7.87–7.79 (m, 2H), 7.80 (d, J=8.2 Hz, 2H, H-2, H-6), 7.66 (d, J=8.2 Hz, 1H), 7.62 (d, J=8.1 Hz, 1H), 7.52 (d, J=8.4 Hz, 2H, H-3, H-5), 7.50 (m, 1H), 7.08 (d, J=16.4 Hz, 1H, vinyl H), 6.96 (d, J=16.4 Hz, 1H, vinyl H), 6.60 (s, 1H), 6.20 (t, J=4.3 Hz, 1H, H-7'), 2.49 (d, J=4.3 Hz, 2H, H-6'), 1.45 (s, 3H, CH$_3$), 1.40 (s, 3H, CH$_3$). Anal. Calcd for C$_{30}$H$_{23}$NO$_2$.0.5 H$_2$O.HCl: C,75,54; H, 5.71; N, 2.94. Found: C, 75.74; H, 5.79; N, 2.56.

EXAMPLE 20

4-[(E)-(5,6-Dihydro-5,5-dimethyl-8-(2-benzothiophenyl)-2-naphthalenyl)-ethenyl]benzoic Acid The title material was prepared as described in Example 1 using tributyl(2-benzothiophenyl)tin.

Methyl 4-[(E)-(5,6-dihydro-5,5-dimethyl-8-(2-benzothiophenyl)-2-naphthalenyl)ethenyl]benzoate $^1$H NMR 400 MHz (CDCl$_3$) δ (ppm): 7.99 (d, J=8.4 Hz, 2H, H-2, H-6), 7.87 (d, J=7.6 Hz, 1H, H-4 or H-7 in benzothiophene), 7.80 (d, J=7.6 Hz, 1H, H-4 or H-7 in benzothiophene), 7.62 (d, J=1.6 Hz, 1H, H-1'), 7.52 (d, J=8.4 Hz, 2H, H-3, H-5), 7.51 (dd, J=8.0, 1.7 Hz, 1H, H-3'), 7.41 (d, J=8.0 Hz, 1H, H-4'), 7.41–7.34 (m, 2H, H-5, H-6 in benzothiophene), 7.34 (s, 1H, H-3 in benzothiophene), 7.16 (d, J=16.3 Hz, 1H, vinyl H), 7.02 (d, J=16.3 Hz, 1H, vinyl H), 6.36 (t, J=4.8 Hz, 1H, H-7'), 3.91 (s, 3H, CO$_2$CH$_3$), 2.41 (d, J=4.8 Hz, 2H, H-6'), 1.38 (s, 6H, 2× CH$_3$).

4-[(E)-(5,6-Dihydro-5,5-dimethyl-8-(2-benzothiophenyl)-2-naphthalenyl)ethenyl]benzoic Acid IR (KBr) υ$_{max}$ (cm$^{-1}$): 3300–2200 (br, s, CO$_2$H, aromatic, aliphatic), 1675 (s, C=O), 1605 (s, C=C). $^1$H NMR 400 MHz (DMSO-d$_6$) δ (ppm): 7.96 (d, J=7.8 Hz, 1H), 7.87 (m, 1H), 7.86 (d, J=8.0 Hz, 2H, H-2, H-6), 7.67 (m, 1H), 7.67 (d, J=8.3 Hz, 2H, H-3, H-5), 7.57 (s, 1H), 7.48 (s, 1H), 7.46 (d, J=8.1 Hz, 1H), 7.42–7.36 (m, 3H), 7.17 (d, J=16.4 Hz, 1H, vinyl H), 6.38 (t, J=4.6 Hz, 1H, H-7'), 2.36 (d, J=4.7 Hz, 2H, H-6'), 1.30 (s, 6H, 2× CH$_3$). Anal. Calcd for C$_{29}$H$_{24}$SO$_2$.0.5 H$_2$O: C,78.17; H, 5,66. Found: C, 78.18; H, 5,69.

EXAMPLE 21

4-[(E)-(5,6-Dihydro-5,5-dimethyl-8-(5-pyrimidyl)-2-naphthalenyl)ethenyl]benzoic Acid The title material was prepared as described in Example 1 using tributyl(5-pyrimidyl)tin.

Methyl 4-[(E)-(5,6-dihydro-5,5-dimethyl-8-(5-pyrimidyl)-2-naphthalenyl)-ethenyl]benzoate $^1$H NMR 400 MHz (CDCl$_3$) δ (ppm): 9.24 (s, 1H, H-2 in pyrimidine), 8.78 (s, 2H, H-4 and H-6 in pyrimidine), 7.99 (d, J=8.3 Hz, 2H, H-2, H-6), 7.50 (d, J=8.4 Hz, 2H, H-3, H-5), 7.48 (dd, J=8.0, 1.6 Hz, 1H, H-3'), 7.42 (d, J=8.0 Hz, 1H, H-4'), 7.09 (d, J=16.3 Hz, 1H, vinyl H), 7.01 (d, J=1.5 Hz, 1H, H-1'), 6.95 (d, J=16.3 Hz, 1H, vinyl H), 6.12 (t, J=4.6 Hz, 1H, H-7'), 3.91 (s, 3H, CO$_2$CH$_3$), 2.43 (d, J=4.7 Hz, 2H, H-6'), 1.37 (s, 6H, 2× CH$_3$).

4-[(E)-(5,6-Dihydro-5,5-dimethyl-8-(5-pyrimidyl)-2-naphthalenyl)ethenyl]benzoic Acid IR (KBr) υ$_{max}$ (cm$^{-1}$): 3300–2100 (br, s, CO$_2$H, aromatic, aliphatic), 1715,1675 (s, C=O), 1605 (s, C=C). $^1$H NMR 400 MHz (DMSO-d$_6$) δ (ppm): 9.22 (s, 1H, H-2 in pyrimidine), 8.80 (s, 2H, H-4 and H-6 in pyrimidine), 7.87 (d, J=8.3 Hz, 2H, H-2, H-6), 7.65 (d, J=8.3 Hz, 2H, H-3, H-5), 7.63 (dd, J=8.1, 1.4 Hz, 1H, H-3'), 7.45 (d, J=8.1 Hz, 1H, H-4'), 7.34 (d, J=16.4 Hz, 1H, vinyl H), 7.15 (d, J=16.4

Hz, 1H, vinyl H), 7.05 (d, J=1.4 Hz, 1H, H-1'), 6.21 (t, J=4.6 Hz, 1H, H-7'), 2.37 (d, J=4.6 Hz, 2H, H-6'), 1.31 (s, 6H, 2× $CH_3$). Anal. Calcd for $C_{29}H_{24}SO_2 \cdot 0.5\ H_2O$: C, 78.17; H, 5.66. Found: C, 78.18; H, 5.69.

EXAMPLE 22

4-[(E)-(5,6-Dihydro-5,5-dimethyl-8-4-methoxyphenyl)-2-naphthalenyl)-ethenyl]benzoic Acid

The title material was prepared as described in Example 1 using tributyl(4-methoxyphenyl)tin.
Methyl 4-[(E)-(5,6-dihydro-5,5-dimethyl-8-4-methoxyphenyl)-2-naphthalenyl)-ethenyl]benzoate $^1$H NMR 400 MHz (CDCl$_3$) δ (ppm): 1.36 (6H, s, 2× —CH$_3$), 2.36 (2H, d, J=4.7 Hz, H-6'), 3.89 (3H, s, —OCH$_3$), 3.92 (3H, s, —OCH$_3$), 5.98 (1H, t, J=4.7 Hz, H-7'), 6.96 (1H, d, J=16.3 Hz, vinyl H), 6.94–6.98 (2H, m, H-3 and H-5 of p-MeOphenyl), 7.11 (1H, d, J=16.3 Hz, vinyl H), 7.19 (1H, d, J=1.7 Hz, H-1'), 7.31–7.33 (2H, m, H-2 and H-6 of p-MeOphenyl), 7.38 (1H, d, J=8.0 Hz, H-4'), 7.44 (1H, dd, J=8.0 and 1.8 Hz, H-3'), 7.49 (2H, d, J=8.4 Hz, H-3 and H-5), 7.99 (2H, d, J=8.3 Hz, H-2 and H-6).

4-[(E)-(5,6-Dihydro-5,5-dimethyl-8-4-methoxyphenyl)-2-naphthalenyl)ethenyl]benzoic Acid

IR (nujol) $υ_{max}$ (cm$^{-1}$): 2920, 2850 (aromatic, aliphatic), 1675 (s, C=O), 1600 (s, C=C). $^1$H NMR 400 MHz (DMSO-d$_6$) δ (ppm): 1.30 (6H, s, 2× —CH$_3$), 2.31 (2H, d, J=4.6 Hz, H-6'), 3.81 (3H, s, —OCH$_3$), 5.96 (1H, d, J=4.6 Hz, H-7'), 7.00 (2H, J=8.7 Hz, H-3 and H-5 of p-MeOphenyl), 7.08 (1H, d, J=17.3 Hz, vinyl H), 7.10 (1H, d, H-1'), 7.27 (2H, d, J=8.8 Hz, H-2 and H-6 of p-MeOphenyl), 7.30 (1H, d, J=17.4 Hz, vinyl H), 7.42 (1H, d, J=8.1 Hz, H-4'), 7.59 (1H, dd, J=8.1 and 1.6 Hz, H-3'), 7.67 (2H, d, J=8.4 Hz, H-3 and H-5), 7.87 (2H, d, J=8.4 Hz, H-2 and H-6). Anal. Calcd for $C_{28}H_{26}O_3$: C, 81.92; H, 6.38. Found: C, 81.75; H, 6.30.

EXAMPLE 23

4-[(E)-(5,6-Dihydro-5,5-dimethyl-8-4-benzyloxyphenyl)-2-naphthaenyl-ethenyl]benzoic Acid

The title material was prepared as described in Example 1 using tributyl(4-benzyloxyphenyl)tin.
Methyl 4-[(E)-(5,6-dihydro-5,5-dimethyl-8-4-benzyloxyphenyl)-2-naphthalenyl)-ethenyl]benzoate $^1$H NMR 400 MHz (CDCl$_3$) δ (ppm): 1.35 (6H, s, 2× —CH$_3$), 2.36 (2H, d, J=4.7 Hz, H-6'), 3.92 (3H, s, —OCH$_3$), 5.15 (2H, s, —OCH$_2$Ph), 5.98 (1H, t, J=4.6 Hz, H-7'), 6.96 (1H, d, J=16.3 Hz, vinyl H), 7.05 (2H, d, J=8.6 Hz, H-3 and H-5 of p-OBn-phenyl), 7.11 (1H, d, J=16.3 Hz, vinyl H), 7.20 (1H, d, J=1.4 Hz, H-1'), 7.32 (2H, H-2 and H-6 of p-OBn-phenyl), 7.36–7.45 and 7.49–7.52 (9H, 2 sets of m, H-3, H-5, H-3', H-4', phenyl), 7.99 (2H, d, J=8.3 Hz, H-2 and H-6).

4-[(E)-(5,6-Dihydro-5,5-dimethyl-8-4-benzyloxyphenyl)-2-naphthalenyl)-ethenyl]benzoic Acid

IR (nujol) $υ_{max}$ (cm$^{-1}$): 2950, 2850 (aromatic, aliphatic), 1675 (C=O), 1605 (C=C). $^1$H NMR 400 MHz (DMSO-d$_6$) δ (ppm): 1.30 (6H, s, 2× —CH$_3$), 2.31 (2H, d, J=4.4 Hz, H-6'), 5.16 (2H, s, —OCH$_2$Ph), 5.97 (1H, t, J=4.5 Hz, H-7'), 7.06–7.51 (13H, 5 sets of m, H-1', H-4', vinyl H, H-2, H-3, H-5, H-6 of BnOphenyl, phenyl), 7.60 (1H, br d, J=7.8 Hz, H-3'), 7.67 (2H, d, J=8.2 Hz, H-3 and H-5), 7.88 (2H, d, J=8.3 Hz, H-2 and H-6). Anal. Calcd for $C_{34}H_{30}O_3$: C, 83.92; H, 6.21. Found: C, 84.00; H, 5.80.

Following the general procedures of Examples 1–23 above, the additional compounds were prepared (X=—CH=CH—).

| Ex. No. | R | Mol. Form. | Microanalysis | | |
|---|---|---|---|---|---|
| | | | | C | H | N |
| 24 | (2-thienyl) | $C_{25}H_{22}O_2S$ | Calc'd. | 77.69 | 5.74 | |
| | | | Found: | 77.53 | 5.74 | |
| 25 | (2-furyl) | $C_{25}H_{22}O_3$ | Calc'd. | 81.06 | 5.99 | |
| | | | Found: | 82.01 | 6.04 | |
| 26 | (isoquinolinyl) | $C_{30}H_{25}NO_2 \cdot HCl$ | Calc'd. | 76.99 | 5.60 | 2.99 |
| | | | Found: | 76.65 | 5.99 | 2.88 |
| 27 | H | $C_{21}H_{20}O_2$ | Calc'd. | 82.87 | 6.62 | |
| | | | Found: | 82.71 | 6.21 | |
| 28 | 3-OMe-phenyl | $C_{28}H_{26}O_3$ | Calc'd. | 81.92 | 6.38 | |
| | | | Found: | 81.70 | 5.98 | |
| 29 | 3-HO-phenyl | $C_{27}H_{24}O_3 \cdot 0.3\ H_2O \cdot 0.05\ CH_3CN$ | Calc'd. | 80.58 | 6.18 | |
| | | | Found: | 80.47 | 6.41 | |
| 30 | 4-OH-phenyl | $C_{27}H_{24}O_3 \cdot 0.1\ H_2O \cdot 0.1\ CH_3CN$ | Calc'd. | 81.19 | 6.14 | |
| | | | Found: | 81.16 | 6.04 | |

-continued

[Structure: tetrahydronaphthalene with R group, X linker, and phenyl-CO2H, with gem-dimethyl]

| Ex. No. | R | Mol. Form. | Calc'd/Found | C | H | N |
|---|---|---|---|---|---|---|
| 31 | 4-CO2H-phenyl | C28H24O4 0.1 H2O 0.05 THF | Calc'd. Found: | 78.79 78.62 | 5.77 5.23 | |
| 32 | 3-CO2H-phenyl | C28H24O4 0.5 H2O 0.05 THF | Calc'd. Found: | 77.49 77.36 | 5.86 5.84 | |
| 33 | 4-NMe2-phenyl | C29H29NO2 0.2 THF | Calc'd. Found: | 81.72 81.53 | 7.04 7.06 | 3.20 3.14 |
| 34 | 4-NH2-phenyl | C27H25NO2 | Calc'd. Found: | 81.99 81.51 | 6.37 5.87 | |
| 35 | 4-COCH3-phenyl | C29H26O3 0.2 THF 0.05 CH3CN | Calc'd. Found: | 81.80 81.58 | 6.37 6.25 | |
| 36 | 4-CONMe2-phenyl | C30H29NO3 | Calc'd. Found: | 79.79 80.34 | 6.47 6.45 | 3.10 3.05 |
| 37 | 4-CF3-phenyl | C28H23F3O2 | Calc'd. Found: | 74.98 74.81 | 5.17 5.13 | |
| 38 | 4-CN-phenyl | C28H23NO2 0.1 H2O 0.1 THF | Calc'd. Found: | 82.29 82.17 | 5.84 5.27 | 3.38 3.07 |
| 39 | methylenedioxyphenyl | C28H24O4 0.1 CH3CN | Calc'd. Found: | 79.02 79.02 | 5.72 5.49 | |
| 40 | 3-NH2-phenyl | C27H25NO2 0.5 H2O 0.3 CH3CN | Calc'd. Found: | 79.53 79.37 | 6.51 5.81 | 4.37 4.39 |

Biological Activity

Prevention of Surgical Adhesions

Models of peritoneal adhesions induced by surgical trauma have been used to predict the clinical activity of a number of marketed anti-adhesion barrier devices. One such model is the trauma-induced caecal adhesion model in rats. A representative retinoid antagonist compound of the present invention, 4-[[(E)-(5,6-dihydro-5,5-dimethyl-8-phenyl)-2-naphthalenyl]vinyl]benzoic acid of the formula

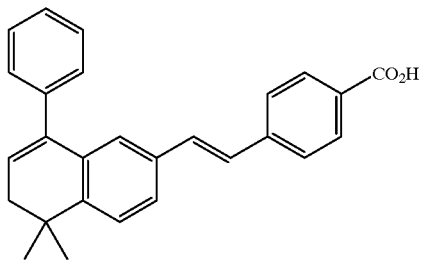

[referred to below as compound A] was used with this model to demonstrate efficacy.

Adult female Wistar rats were used in our studies. The trauma induction was carried out using aseptic conditions in animals anesthetized with a mixture of Ketamine (100 mg/kg) and Rompun (10 mg/kg) given IP. A 2 cm midline abdominal incision was made and the caecum was exteriorized. Both sides of the caecum were abraded with a dry gauze until there was evidence of punctate bleeding. After replacing the organ in the abdominal cavity, the incision was closed. Trauma to the caecum produces fibrous scar tissue or adhesions to adjacent organs, peritoneal wall, or the omentum. Animals were treated with test compound orally or by intravenous injection or intra-abdominally by direct instillation into the peritoneal cavity. Oral treatments were administered once daily for up to 7 days. Intra-abdominal treatments were applied once post-trauma and just prior to wound closure.

On the seventh postoperative day, the animals were sacrificed and the peritoneal cavity was exposed and examined for adhesions. Three criteria that were used to evaluate the adhesions are: severity of the adhesions, extent or area of the ceacum involved with adhesions and the number of adhesions formed in each animal. Statistical analysis of the data was performed using students' T test. The following scoring system was used:

| Grade | Description |
|---|---|
| 0 = | no adhesions; |
| 1.0 = | easily separable, filmy, non-vascularized. adhesions covering 25% of the caecum; |
| 2.0 = | dense adhesions separated by blunt dissection and involving 50% of the caecum; |
| 3.0 = | dense, fibrous, vascularized adhesions requiring sharp dissection and covering 75% of the caecum; |
| 4.0 = | severe, dense, vascularized adhesions unable to separate without tearing the adjacent membranes and covering greater than 75% of the caecum. |

The test compound administered orally for 7 days had a significant dose-dependent effect on the number and severity of adhesions formed. FIG. 1 shows that compared to the vehicle control, the test compound A significantly reduced the number and severity of adhesions per animal at 10 and 15 mg/kg.

A comparison of all-trans retinoic acid (RA) and representative retinoid antagonist compounds of the present invention on the number of, severity and extent of caecal adhesions is shown in table I. All-trans retinoic acid, the triple agonist, tested at twice the dose of the above-described test compound demonstrated no significant effect on trauma induced adhesions. In constrast, retinoid antagonists Compound B and Compound D dose-dependently reduced adhesion number and severity.

TABLE 1

(Comparison of Orally Administered Retinoid Antagonists Compound B & D to All Trans Retinoic Acid)

| Treatment | Dose (mg/kg) | Mean # of Adhesions per Rat +/−SEM | Mean Adhesion Severity Grade per Rat +/−SEM |
|---|---|---|---|
| Vehicle Control | | 3.8 ± 0.8 | 8.0 ± 1.7 |
| Compound B | 0.5 | 3.8 ± 0.7 | 7.4 ± 1.7 |
| Compound B | 5.0 | 1.8 ± 0.6 | 3.6 ± 1.5 |
| Compound B | 10.0 | 1.2 ± 0.7* | 1.8 ± 1.3* |
| Vehicle Control | | 7.6 ± 0.9 | 21.2 ± 2.8 |
| Compound D | 1.0 | 6.0 ± 0.8 | 14.2 ± 2.7 |
| Compound D | 3.0 | 2.8 ± 0.8* | 6.0 ± 1.6* |
| Compound D | 10.0 | 2.2 ± 0.6* | 4.6 ± 1.0* |
| Compound D | 15.0 | 2.4 ± 0.7* | 5.0 ± 1.5* |
| Vehicle Control | | 7.5 ± 0.6 | 16.25 ± 1.7 |
| All Trans Retinoic Acid | 1.0 | 7.8 ± 0.9 | 20.2 ± 2.0 |
| All Trans Retinoic Acid | 10.0 | 5.6 ± 0.8 | 13.8 ± 2.5 |
| All Trans Retinoic Acid | 30.0 | 6.6 ± 0.9 | 16.8 ± 2.2 |

*p = 0.005

The test compound described above administered by the intra-abdominal route was compared to some other representative retinoid antagonists of the present invention. A single dose of compound in 3 ml volume was instilled over the traumatized caecum and abdominal cavity prior to closing the incision. Seven days later the animals were sacrificed and the abdominal cavity was examined for adhesions to the caecum. Compared to the vehicle control, a single intra-abdominal application of compound A at 5 mg significantly reduced the number of adhesions formed. At this dose compound A also effectively reduced the severity of caecal adhesions as illustrated by the results in table 2. Each of the other compounds tested also showed significant reduction in the number and severity of adhesions formed.

TABLE 2

(Effect of Retinoid Antagonist Compounds following a single intra-abdominal treatment in the trauma-induced caecal adhesion in rats)

| Treatment | Dose (mg/kg) | Mean # of Adhesions per Rat +/−SEM | Mean Adhesion Severity Grade per Rat +/−SEM |
|---|---|---|---|
| Vehicle Control | | 6.6 ± 0.8 | 8.4 ± 1.1 |
| Compound A | 0.5 | 6.4 ± 0.9 | 8.4 ± 1.5 |
| Compound A | 2.0 | 4.2 ± 1.3 | 5.6 ± 2.2 |
| Compound A | 5.0 | 2.3 ± 0.75* | 2.3 ± 0.75* |
| Vehicle Control | | 6.4 ± 0.2 | 1.3 ± 0.4 |
| Compound B | 0.5 | 5.8 ± 1.4 | 11.2 ± 3.2 |
| Compound B | 1.5 | 2.2 ± 0.5* | 4.2 ± 1* |
| Compound B | 5.0 | 2.4 ± 0.8* | 4.8 ± 1.9* |
| Vehicle Control | | 7.8 ± 0.5 | 18.4 ± 0.8 |
| Compound C | 0.3 | 6.3 ± 0.3 | 21.3 ± 2.3 |
| Compound C | 1.0 | 5.5 ± 0.9 | 13 ± 2.1* |
| Compound C | 3.0 | 5.8 ± 0.8 | 14.2 ± 01.1* |
| Vehicle Control | | 6.0 ± 0.8 | 16.6 ± 1.6 |
| Compound D | 0.3 | 6.2 ± 0.7 | 13.4 ± 1.7 |
| Compound D | 1.0 | 3.2 ± 0.6* | 6.4 ± 1.3* |
| Compound D | 3.0 | 2.0 ± 0.3* | 3.6 ± 0.8* |

TABLE 2-continued (Effect of Retinoid Antagonist Compounds following a single intra-abdominal treatment in the trauma-induced caecal adhesion in rats)

| Treatment | Dose (mg/kg) | Mean # of Adhesions per Rat +/−SEM | Mean Adhesion Severity Grade per Rat +/−SEM |
|---|---|---|---|
| Vehicle Control | | 8.0 ± 1.9 | 18.8 ± 1.9 |
| Compound E | 0.3 | 6.5 ± 0.6 | 20.3 ± 1.3 |
| Compound E | 1.0 | 7.5 ± 0.3 | 20 ± 1.1* |
| Compound E | 3.0 | 4.40 ± 1.1* | 9.6 ± 2.4* |

*p = 0.01

Structures of test compounds:

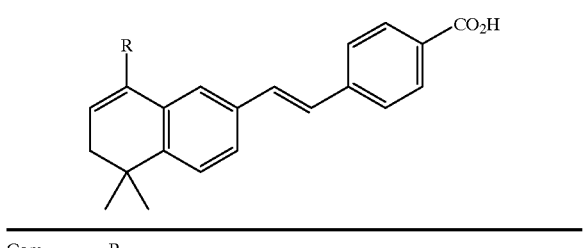

Compound A   R = 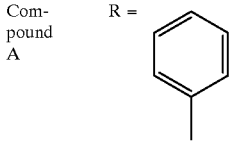

Compound B   R = 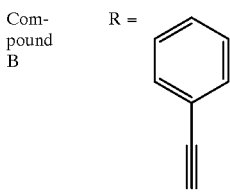

Compound C   R = 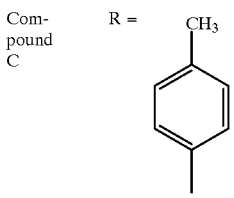

Compound D   R = 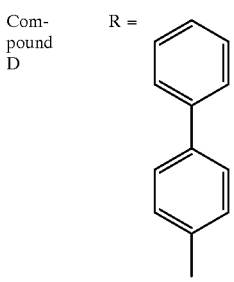

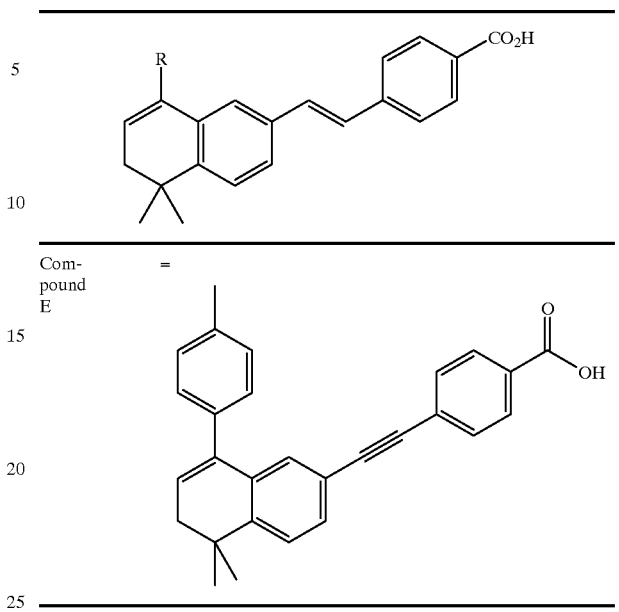

Compound E =

As shown above the compounds of the present invention are useful in the prevention of post-surgical adhesions.

For prevention of surgical adhesions, the retinoid antagonist may be administered by a variety of systemic and local methods. The compounds may be administered orally, by intravenous injection, by intramuscular injection or by intracavity instillation. The general range of doses will depend on the efficacy of each compound and the intended route but is expected to be from 0.1 mg/kg to 100 mg/kg with a preferred range of 1 to 25 mg/kg. Preferred routes of administration are oral administration or direct administration (intracavity instillation) to a site of surgical activity on an organ surface.

The term of administration may vary depending upon a number of factors which would be readily appreciated by those skilled in the art. In general, administration of a retinoid antagonist of the present invention should be effected 12–48 hours prior to the time of surgery and for at least 24–48 hours post-surgery. In general the retinoid antagonist may be administered from 72 hours prior to surgery and continue up to 2 weeks after surgery and preferably for a period 12 hours prior to surgery and continuing 48 hours after surgery.

For intracavity administration the retinoid can be administered in a suitable vehicle such as 5% dextrose in water adjusted to a pH to assure complete salt formation. However it is understood that many other single dose delivery systems could be contemplated by those skilled in the art including microcapsules, microspheres, liposomes, viscous instilates, and polymeric delivery materials.

The retinoid antagonists of formula II above may be used topically or systemically, as anticancer agents and in the treatment, amelioration or prevention of the skin disorders and rheumatic illnesses (including rheumatoid arthritis) described in EP 661,259 A1 and in U.S. Pat. No. 5,618,839. In this regard they may be used for therapy in animals, including humans, of premalignant epithelial cell lesions, as a prophylaxis against tumor promotion in epithelial cells and treatment for dermatoses such as ichthyoses, follicular disorders, benign epithelial disorders and other proliferative skin diseases such as acne, psoriasis, eczema, atopic dermatitis, non-specific dermatosis and the like. They may also be used in reversing and preventing the effects of irradiation damage to skin. When used for the above purposes, they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, orbital, mannitol, gum acacia, alginates, cellulose, talc, magnesium stearate, polyoxyethylene sorbitan monolaurate, and other commonly used pharmaceutical carries. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases such as treatment of severe cystic acne, oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspension, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitable administered at the rate of 100 µg to 100 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 1 mg to about 25 mg of active substance.

U.S. Pat. No. 4,876,381 issued on Oct. 24, 1989 to Lang et al. provides examples of formulations constituting gel, unguent, powder, cream, etc. for a retinoid compound. The aforesaid U.S. patent can be used as a guide to formulate a compound of formula I and is herein incorporated by reference in its entirety.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the Physicians's Desk Reference, 47th Edition, 1993, published by Medical Economics Data. The compounds of formula II may also be used to treat severe recalcitrant cystic acne or severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 10 µg to 10 mg per day per kg of body weight; a preferred method of administration consists of using solutions or suspensions containing approximately from 0.01 mg to 1 mg of active substance per ml.

Several retinoids have been found to possess anti-tumor properties. Roberts, A. B. and Sporn, M. B. in "The Retinoids", Sporn, M. B., Roberts, A. B., and Goodman, D. S., eds, 1984, 2 pp. 209–286, Academic Press, New York; Lippman, S. M., Kessler, J. F., and Meyskens, F. L., Cancer Treat. Rep., 1987, 71, p. 391; ibid., p. 493. As used herein, the term "anti-tumor" includes both chemopreventative (prophylactic or tumor promotion inhibiting) and therapeutic (curative) use. For example, all-trans retinoic acid can be used to treat acute promyelocytic leukemia. Huang, M. Et al., Blood 1988, 72, p. 567. Isotretinoin has been shown to be useful in prevention of second primary tumors in squamous-cell carcinoma of the head and neck. Hong, W. K. et al., N. Engl. J. Med., 1990, 323, p. 795.

The compounds of formula II can also be used in substantially the similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula II in squamous-cell carcinoma of the head and neck, an oncologist may refer to the study by Hong, W. K. et al. in N. Engl. J. Med., 1990, 323, p. 795. For treating acute promyelocytic leukemia, the oncologist may refer to the study by Huang, M. et al. in Blood, 1988, 72, p. 567.

We claim:

1. A method for the minimization or prevention of post-surgical adhesion formation between organ surfaces comprising administering to an animal host an effective amount of a retinoic acid antagonist for a period of time sufficient to permit tissue repair, wherein the retinoic acid antagonist is a compound of the formula

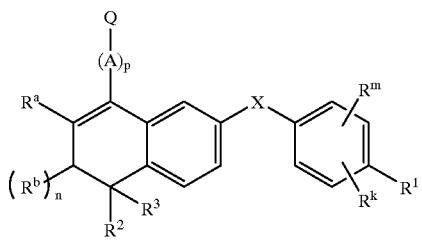

II or nontoxic pharmaceutically acceptable salts, physiologically hydrolyzable esters or solvates thereof, in which X is —O—CO—, —NH—CO—, —CS—NH, —CO—O—, —CO—NH—, —COS—, —SCO—, —SCH$_2$—, —CH$_2$—CH$_2$—, —C(C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$ alkyl, hydroxy, C$_{1-6}$ alkyloxy or nitro;

n is zero or one;

A is —NH(CH$_2$)$_m$—, —S—, —SO—, —SO$_2$—, —O—, —C(C—, —CR$^8$R$^9$, —CR$^8$=CR$^9$—, phenyl, phenyl substituted by a C$_{1-6}$ alkyl, C$_{1-6}$ alkoxy, halogen, CO$_2$R$^8$, —(CH$_2$)$_m$OR$^8$, —(CH$_2$)$_m$NR$^9$R$^8$, or —COR$^{10}$ group, naphthyl, naphthyl substituted by a C$_{1-6}$ alkyl, C$_{1-6}$ alkoxy, halogen, CO$_2$R$^8$, —(CH$_2$)$_m$OR$^8$, —(CH$_2$)$_m$NR$^8$R$^9$ or —COR$^{10}$, or heteroaryl;

Q is phenyl, naphthyl or heteroaryl, said phenyl, naphthyl or heteroaryl group being optionally substituted by one to three same or different C$_{1-6}$ alkyl, C$_{1-6}$ fluoroalkyl, C$_{1-6}$ alkoxy, halogen, CO$_2$R$^{11}$, —(CH$_2$)$_q$OR$^{11}$, —(CH$_2$)$_q$NR$^{11}$R$^{12}$, —NHCOR$^{13}$ or —COR$^{13}$ with the proviso that when A is —S—, —SO—, —SO$_2$— or —O—, then Q is a phenyl, naphthyl or heteroaryl group substituted by one to three halogen, C$_{1-6}$ fluoroalkyl, CO$_2$R$^{11}$, —(CH$_2$)$_q$OR$^{11}$, —(CH$_2$)$_q$NR$^{11}$R$^{12}$, —NHCOR$^{13}$ or —COR$^{13}$;

R$^5$ and R$^6$ are each independently hydrogen or C$_{1-6}$ alkyl;

R$^8$ and R$^9$ are each independently hydrogen or C$_{1-6}$ alkyl;

R$^{10}$ and R$^{13}$ are each independently hydrogen, C$_{1-6}$ alkyl or C$_{1-6}$ fluoroalkyl;

R$^{11}$ and R$^{12}$ are each independently hydrogen or C$_{1-6}$ alkyl;

R$^a$ and R$^b$ are independently hydrogen or C$_{1-6}$ alkyl; but when n is one, R$^a$ and R$^b$ together can form a radical of the formula

Z is hydrogen, C$_{1-6}$ alkyl, benzyl, p-methoxybenzyl, allyl or trimethylsilylethyl;

m and q are independently 0 to 2;

p is 0 or 1 with the proviso that when p is 0 then Q is phenyl, naphthyl or heteroaryl substituted by one to three —(CH$_2$)$_q$OR$^{11}$, —(CH$_2$)$_q$NR$^{11}$R$^{12}$, or —COR$^{13}$;

R$^2$ and R$^3$ are each independently hydrogen or C$_{1-6}$ alkyl;

R$^1$ is —CO$_2$Z, C$_{1-6}$ alkyl, —CH$_2$OH, —CONHR$^7$ or CHO;

R$^7$ is hydrogen or C$_{1-6}$ alkyl;

provided that when X is —C≡C—, A is not —CR$^8$=CR$^9$— or —C≡C—.

2. A method for the minimization or prevention of post-surgical adhesion formation between organ surfaces comprising administering to an animal host an effective amount of a retinoic acid antagonist for a period of time sufficient to permit tissue repair, wherein the retinoic acid antagonist is a compound of the formula

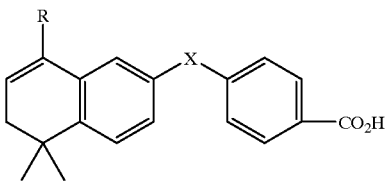

wherein (a) R is 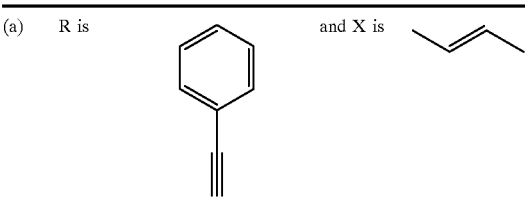

(b) R is 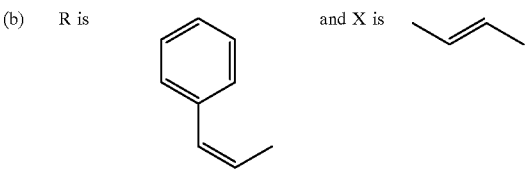

(c) R is 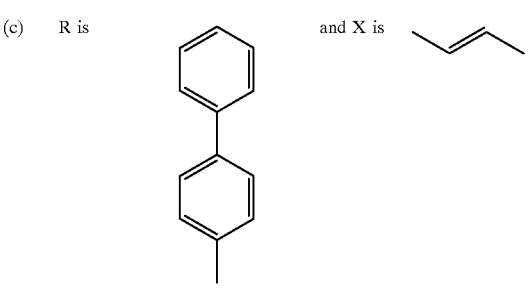

(d) R is 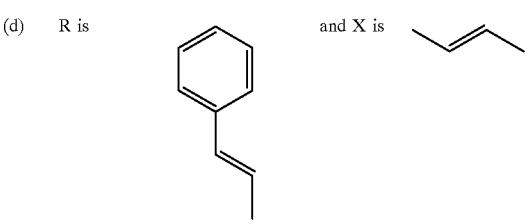

-continued
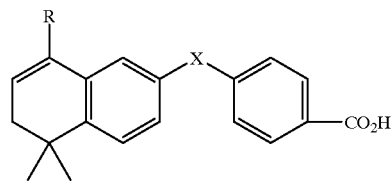
wherein
(e) R is 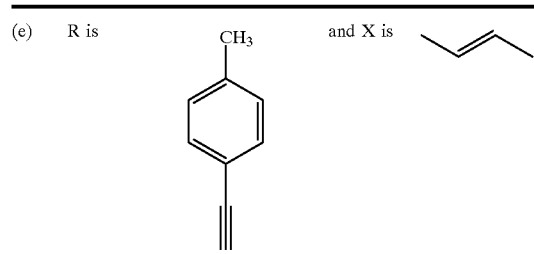 and X is
(f) R is 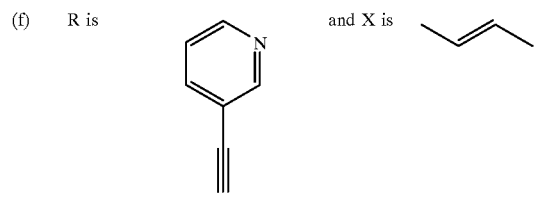 and X is
(g) R is 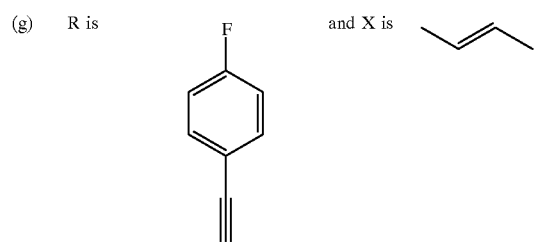 and X is
(h) R is 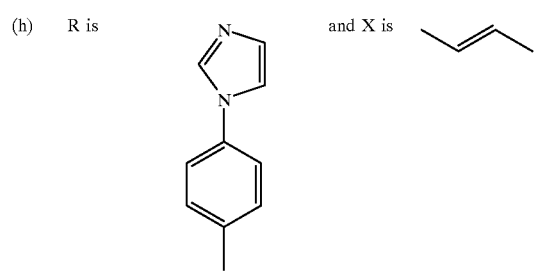 and X is
(i) R is 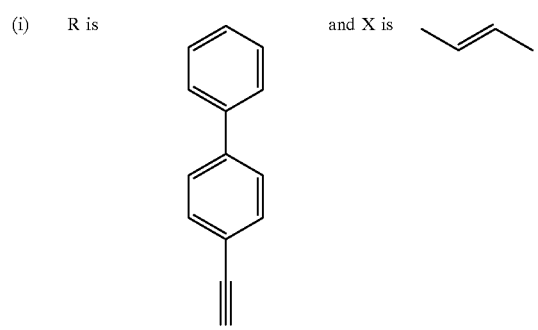 and X is
-continued
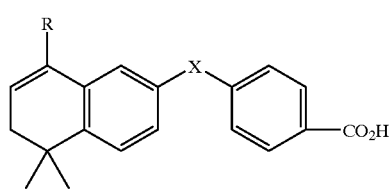
wherein
(j) R is 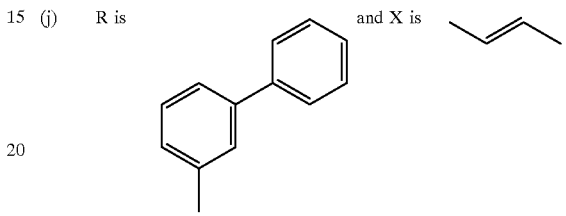 and X is
(k) R is 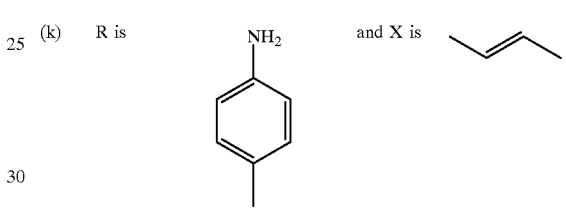 and X is
(l) R is 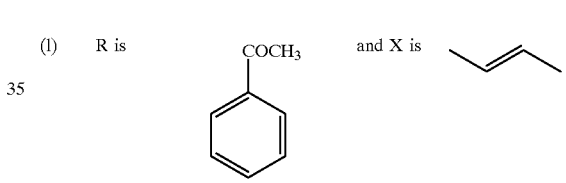 and X is
(m) R is 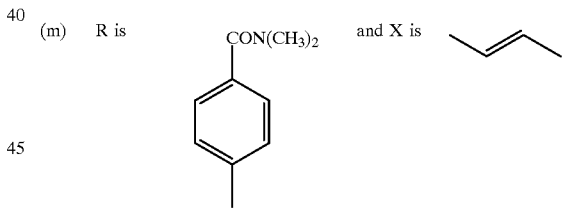 and X is
(n) R is 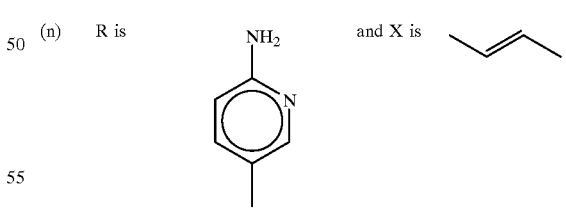 and X is
(o) R is 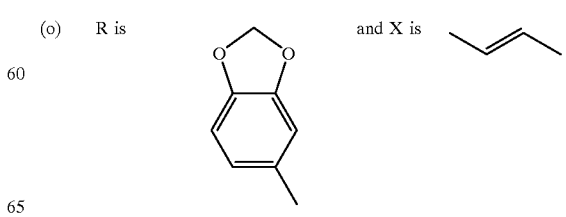 and X is -continued

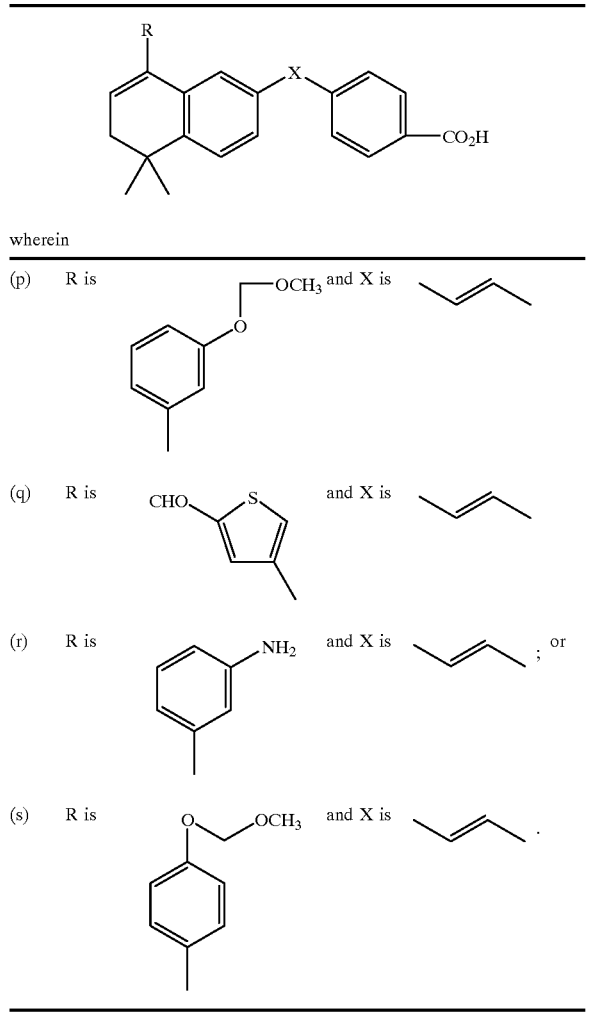

wherein (p) R is [structure with OCH3] and X is [propenyl]

(q) R is [structure with CHO, S, methyl] and X is [propenyl]

(r) R is [structure with NH2] and X is [propenyl]; or (s) R is [structure with O-OCH3] and X is [propenyl].

3. The method of claim 1 wherein the retinoid antagonist is administered orally.

4. The method of claim 1 wherein the retinoid antagonist is administered directly to a site of surgical activity on an organ surface.

5. A method for the minimization or prevention of post-surgical adhesion formation between organ surfaces comprising administering to an animal host an effective amount of a retinoic acid antagonist for a period of time sufficient to permit tissue repair, said retinoic acid antagonist having the formula

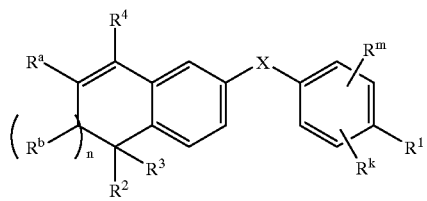

or a nontoxic pharmaceutically acceptable salt, physiologically hydrolyzable ester or solvate thereof, in which
X is —O—CO—, —NH—CO—, —CS—NH, —CO—O—, —CO—NH—, —COS—, —SCO—, —SCH$_2$—, —CH$_2$—CH$_2$—, —C—C, —CH$_2$—NH—, —COCH$_2$—, —NHCS—, —CH$_2$S—, —CH$_2$O—, —OCH$_2$—, —NHCH$_2$— or —CR$^5$=CR$^6$—;
R$^m$ and R$^k$ are independently hydrogen, halogen, C$_{1-6}$ alkyl, hydroxy, C$_{1-6}$alkyloxy or nitro;
n is zero or one;
R$^4$ is —(CH$_2$)$_t$—Y;
R$^1$ is —CO$_2$Z, —C$_{1-6}$ alkyl, CH$_2$OH, —CONHR$^y$ or CHO;
R$^2$ and R$^3$ are independently hydrogen or C$_{1-6}$ alkyl;
R$^a$ and R$^b$ are independently hydrogen or C$_{1-6}$ alkyl; but when n is one, R$^a$ and R$^b$ together can form a radical of the formula

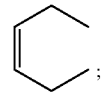;

Y is phenyl or naphthyl and both radicals can be optionally substituted with one to three same or different C$_{1-6}$ alkyl or halogen groups;
Z is hydrogen or C$_{1-6}$ alkyl;
R$^5$, R$^6$ and R$^y$ are independently hydrogen or C$_{1-6}$ alkyl; and
t is zero to six.

6. The method of claim 5 wherein the retinoid antagonist is the compound having the formula

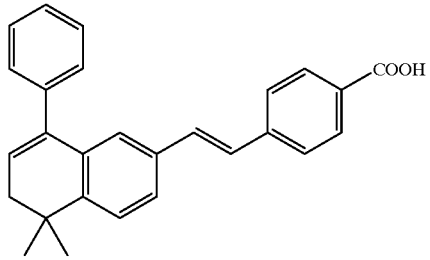

7. The method of claim 5 or claim 6 wherein the retinoid antagonist is administered orally.

8. The method of claim 5 or claim 6 wherein the retinoid antagonist is administered directly to a site of surgical activity on an organ surface.

* * * * *